(12) United States Patent
Kunieda et al.

(10) Patent No.: US 6,307,914 B1
(45) Date of Patent: Oct. 23, 2001

(54) MOVING BODY PURSUIT IRRADIATING DEVICE AND POSITIONING METHOD USING THIS DEVICE

(75) Inventors: Tatsuya Kunieda, Tokyo; Hiroki Shirato, Hokkaido, both of (JP)

(73) Assignees: Mitsubishi Denki Kabushiki Kaisha, Tokyo; Hokkaido University, Hokkaido, both of (JP)

( * ) Notice: Subject to any disclaimer, the term of this patent is extended or adjusted under 35 U.S.C. 154(b) by 0 days.

(21) Appl. No.: 09/452,375

(22) Filed: Dec. 1, 1999

(30) Foreign Application Priority Data

Mar. 12, 1998 (JP) ................................... 10-344423

(51) Int. Cl.$^7$ ............... A61N 5/10; A61B 6/03

(52) U.S. Cl. ................................... 378/65; 378/8

(58) Field of Search .................. 378/16, 65, 8

(56) References Cited

U.S. PATENT DOCUMENTS

| | | | |
|---|---|---|---|
| 5,307,264 | * 4/1994 | Waggener et al. | 378/14 |
| 5,430,308 | 7/1995 | Feichtner et al. | 250/580 |
| 6,029,079 | * 2/2000 | Cox et al. | 600/407 |

FOREIGN PATENT DOCUMENTS 679006A  3/1994  (JP) .

* cited by examiner

*Primary Examiner*—David V. Bruce
(74) *Attorney, Agent, or Firm*—Rothwell, Figg, Ernst & Manbeck

(57) ABSTRACT

A moving body pursuit irradiating device has plural X-ray fluoroscopes for picking up the image of a tumor marker buried in the vicinity of a tumor, and recognition processing sections which execute template matching by a shading normalization mutual correlation method, further calculating three-dimensional coordinates of the tumor marker from the two-dimensional coordinates calculated by the recognition processing sections, and controlling the medical treatment beam of a linac.

14 Claims, 29 Drawing Sheets

FIG. 2A1
FLUOROSCOPIC IMAGE A

FIG. 2B1
FLUOROSCOPIC IMAGE A
(AFTER DIGITIZATION)

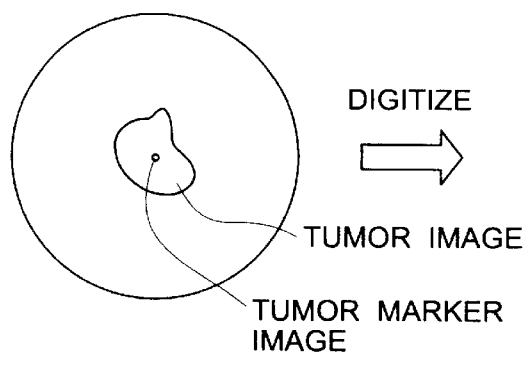

DIGITIZE

TUMOR IMAGE

TUMOR MARKER IMAGE

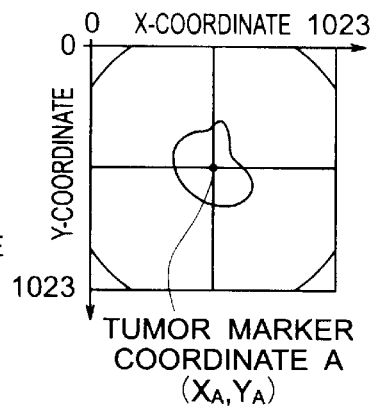

TUMOR MARKER COORDINATE A
$(X_A, Y_A)$

FIG. 2C1

TEMPLATE IMAGE A

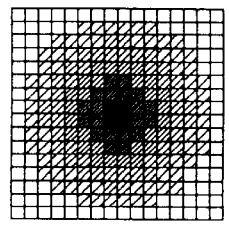

TUMOR MARKER COORDINATE A IS OBTAINED AS A COORDINATE SHOWING A HIGHEST CORRELATION VALUE BY SEARCHING TEMPLATE IMAGE A REGISTERED IN ADVANCE IN FLUOROSCOPIC IMAGE A

FIG. 2A2
FLUOROSCOPIC IMAGE B

FIG. 2B2
FLUOROSCOPIC IMAGE B
(AFTER DIGITIZATION)

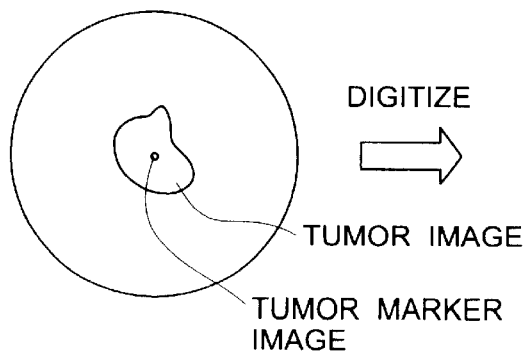

DIGITIZE

TUMOR IMAGE

TUMOR MARKER IMAGE

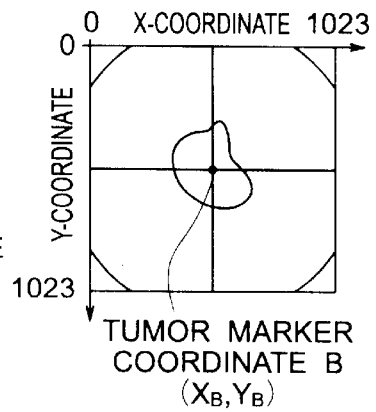

TUMOR MARKER COORDINATE B
$(X_B, Y_B)$

FIG. 2C2

TEMPLATE IMAGE B

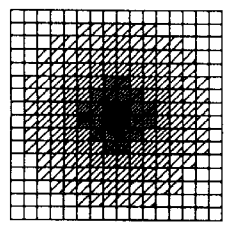

TUMOR MARKER COORDINATE B IS OBTAINED AS A COORDINATE SHOWING A HIGHEST CORRELATION VALUE BY SEARCHING TEMPLATE IMAGE B REGISTERED IN ADVANCE IN FLUOROSCOPIC IMAGE B

FLUOROSCOPIC PASS 1

FLUOROSCOPIC PASS 2

FLUOROSCOPIC PASS 3

FLUOROSCOPIC PASS 4

FIG. 7A
FLUOROSCOPIC IMAGE
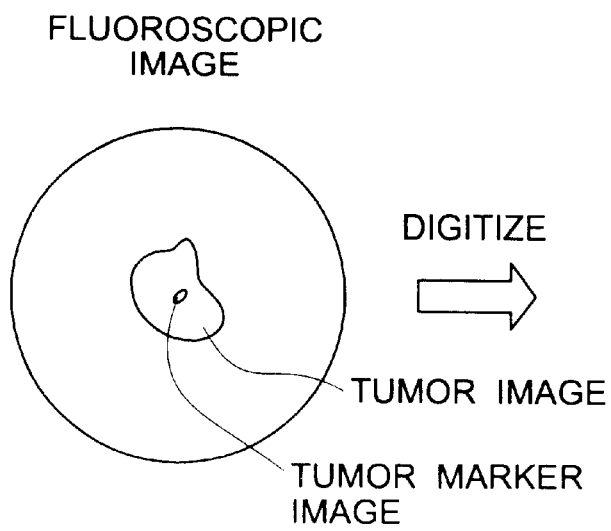
FIG. 7B
FLUOROSCOPIC IMAGE (AFTER DIGITIZATION)
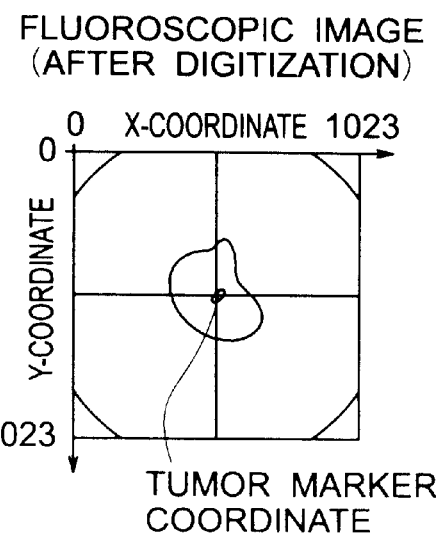
FIG. 7C
TEMPLATE IMAGE
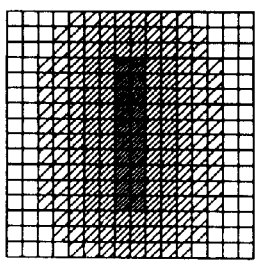
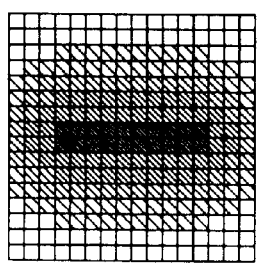
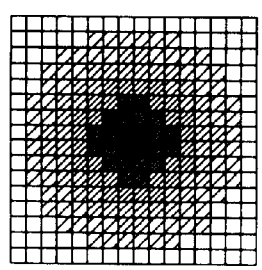
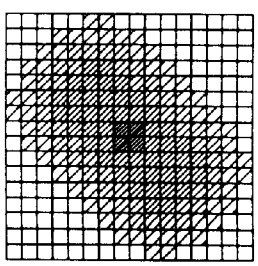
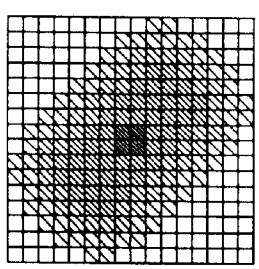

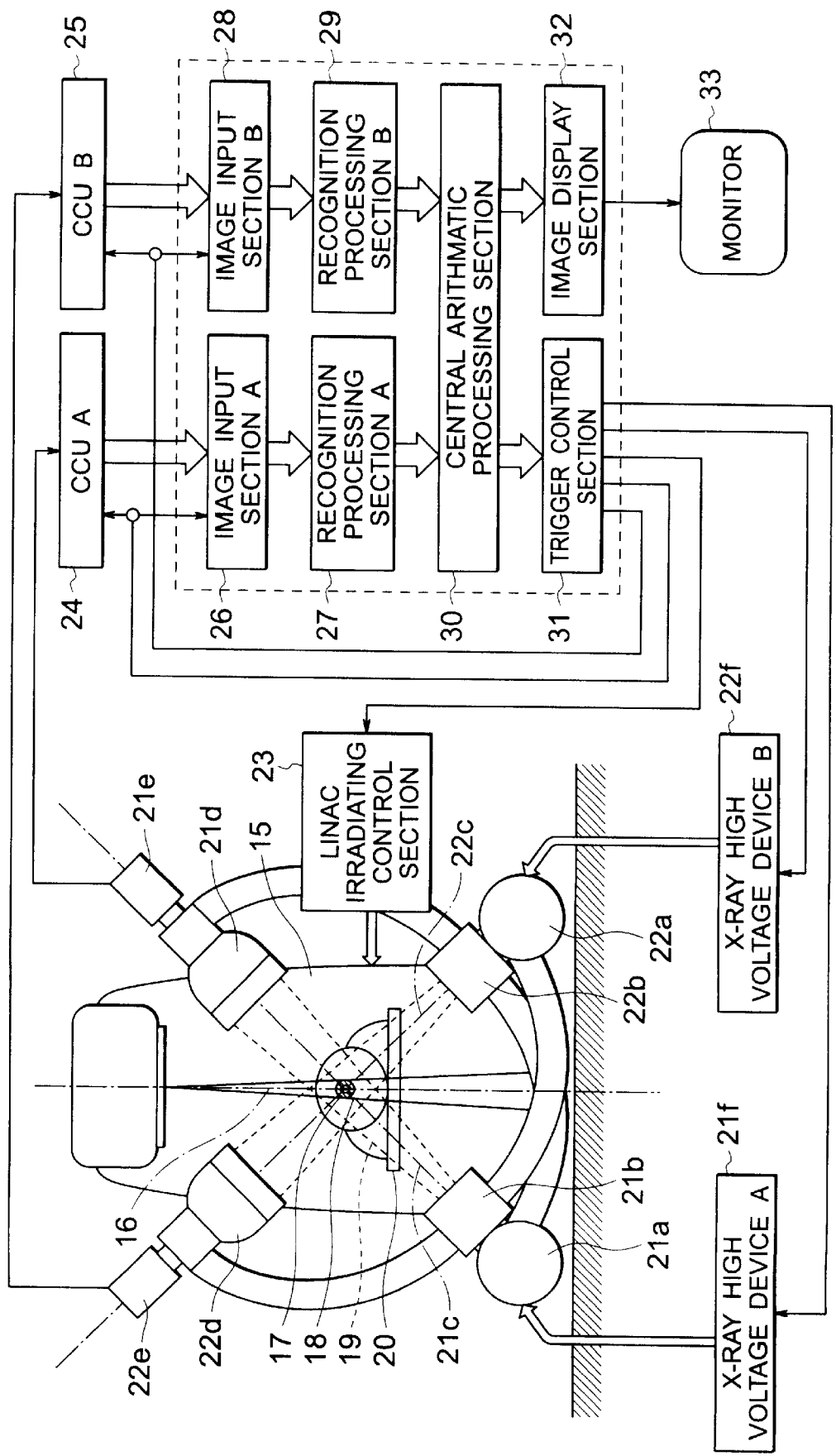

A MOVING AMOUNT REQUIRED TO POSITION A TUMOR PORTION AT A PHYSICAL ISOCENTER IS CALCULATED FROM A LAND MARK POSITION

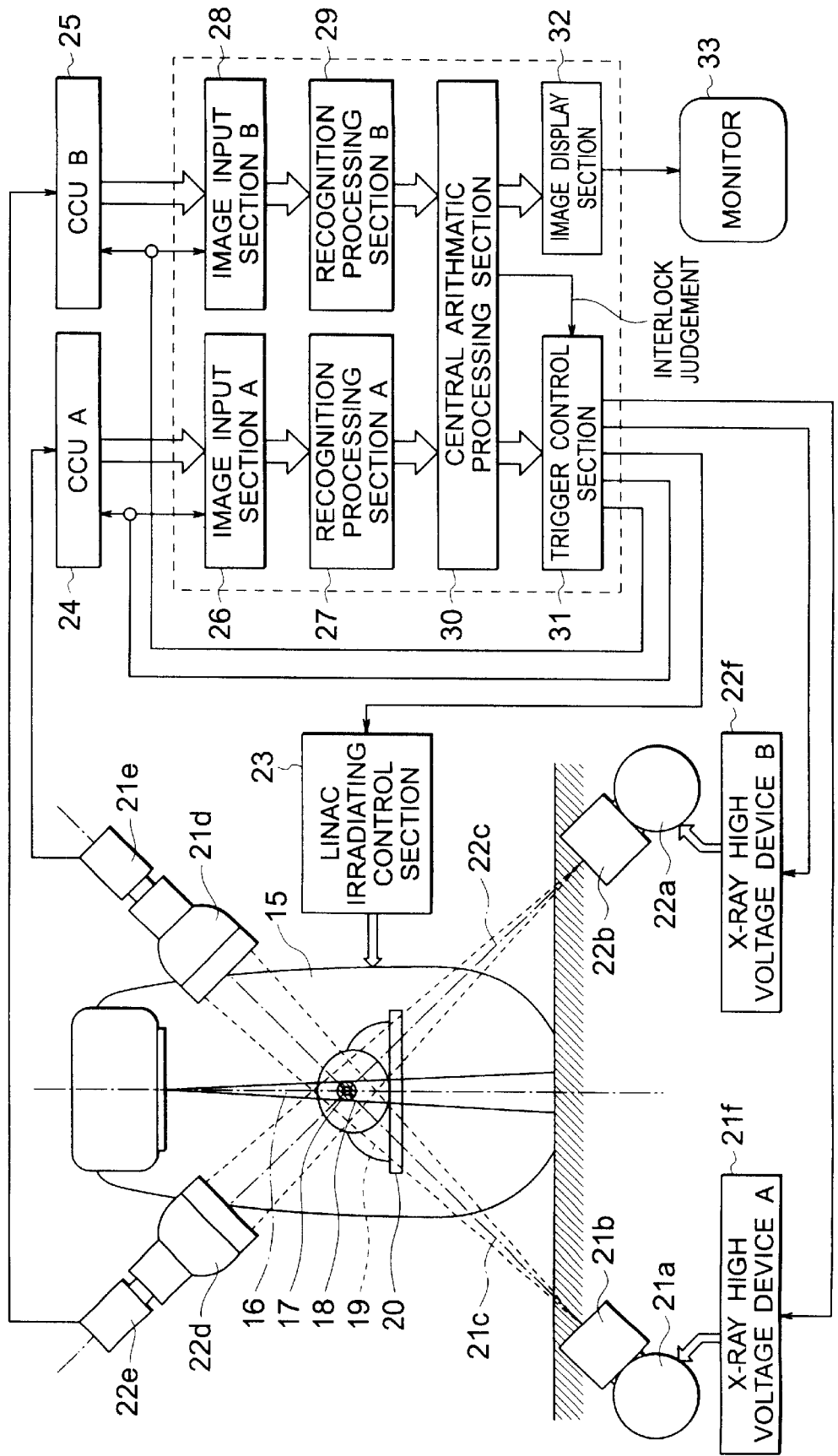

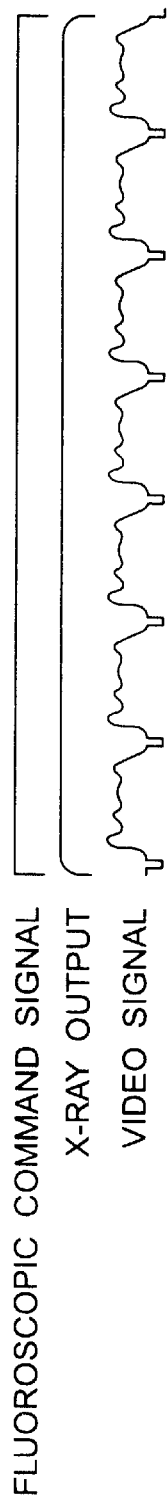
FIG. 15A  CASE OF 30 FRAME/SECOND: OUTPUT X-RAY AT ANY TIME
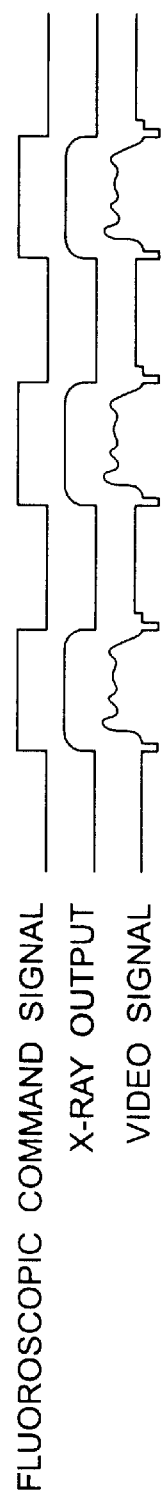
FIG. 15B  CASE OF 15 FRAME/SECOND: X-RAY OUTPUT DUTY IS 50%
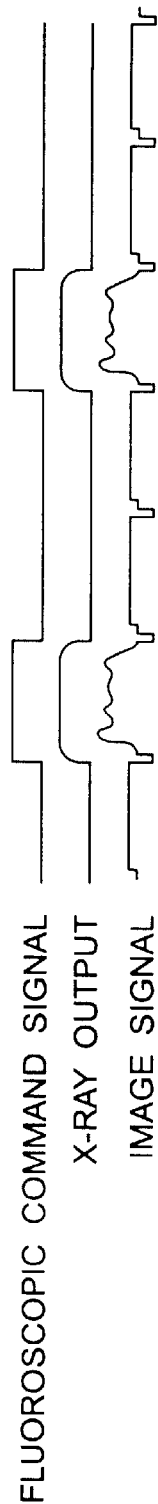
FIG. 15C  CASE OF 10 FRAME/SECOND: X-RAY OUTPUT DUTY IS 33%

MOVING BODY PURSUIT IRRADIATING DEVICE AND POSITIONING METHOD USING THIS DEVICE

BACKGROUND OF THE INVENTION

1. Field of the Invention

This invention relates to a moving body pursuit irradiating device of an X-ray, an electron beam, a proton beam, a heavy particle beam, etc. capable of automatically calculating the position of a tumor moving round within a leading body portion in real time irrespective of absolute accuracy of a mechanical system and accurately selectively irradiating a large dose of beam to the tumor and reducing exposure to a normal tissue, and also to a positioning method using this device.

2. Description of the Related Art

A conventional moving body pursuit irradiating device will be explained with reference to the drawings. FIG. 27 is a view showing the construction of a conventional moving body pursuit irradiating device shown in e.g., Japanese Patent Application Laid-Open No. Hei 1-242074.

In FIG. 27, reference numerals 1, 5 and 6 respectively designate a medical treatment base, a patient and a supporting frame rail. Reference numerals 7 and 8 respectively designate a supporting frame rail and an X-ray TV camera input device. This X-ray TV camera input device 8 is constructed by an X-ray tube 8a arranged in the supporting frame rail 6, and an image intensifier 8b arranged in the supporting frame rail 7. Reference numerals 9, 10 and 11 respectively designate a digital image processor connected to the image intensifier 8b, an electronic computer connected to this digital image processor 9, and a medical treatment base controller connected to the electronic computer 10 and coupled to the medical treatment base 1. Each of reference numerals 12 and 13 designates an image display connected to the electronic computer 10. Reference numeral 14 designates a tablet connected to the electronic computer 10.

An operation of the above conventional moving body pursuit irradiating device will be next explained with reference to the drawings. FIG. 28 is a view for explaining the positional relation of the x-ray tube 8a of the conventional moving body pursuit irradiating device and a diseased part S of the patient 5. FIG. 29 is a view showing an X-ray TV image of the diseased part S.

In FIG. 28, a coordinate axis in a long side direction of the medical treatment base 1 is set to an X-axis, and a coordinate axis in a vertical direction is set to a Z-axis. Further, a direction perpendicular to the X-axis and the Z-axis is set to a Y-axis. An origin O is set to be located just below a center of the medical treatment base 1 and is also set to be located on a vertical line passing the X-ray tube 8a in an initial position A. When the height between the X-ray tube 8a and the medical treatment base 1 is set to H, coordinates in the initial position A are (0, 0, H). An intersecting point of a vertical axis passing a position B and the X-axis just below the medical treatment base 1 is set to Q. The distance between the initial position A of the X-ray tube 8a and the initial position B after parallel displacement in the X-axis direction is set to a.

In FIGS. 29(a) and 29(b), values of the diseased part S of the patient 5 in the initial position A of the X-ray tube 8a and the position B after the parallel displacement are respectively shown by S1 and S2. Coordinate positions of images S1 and S2 of the diseased part S of the patient 5 are expressed at a specific one point (a center of the patient or its peripheral portion) of the diseased part S.

First, an X-ray TV image of the diseased part S of the patient 5 is picked up by the X-ray TV camera input device 8 in the initial position A of the X-ray tube 8a. This X-ray TV image is digitized by the digital image processor 9. Thereafter, an image distortional correction such as bobbin winding distortion, etc. is made and the corrected image is displayed in the image display 12 through the electronic computer 10.

Subsequently, the X-ray tube 8a and the image intensifier 8b are simultaneously moved in parallel with each other by the distance a in the X-axis direction on the supporting frame rails 6, 7. The X-ray TV image of the diseased part S of the patient 5 is again picked up by the X-ray TV camera input device 8 in the position B after the parallel displacement. This X-ray TV image is then displayed in the image display 13 through the digital image processor 9 and the electronic computer 10.

Then, an operator displays (points) images S1 and S2 of the diseased part S in the image displays 12 and 13 by the tablet 14.

The electronic computer 10 executes the following arithmetic operations (1) to (4) on the basis of information of the images S1 and S2 of the supported diseased part S. In this case, a vector between coordinates a and b is shown by "→a·b".

(1) The distance 1 on the X-axis between the images S1 and S2 of the diseased part S is calculated by the difference between vector→O·S1 and vector→O·S2.
(2) A height h of the diseased part S in the Z-axis direction is calculated by h=1·H/(a+1).
(3) When X and Y coordinate values of the image S1 of the diseased part S are respectively set to X1 and Y1 as shown in FIG. 29(a), X, Y and Z coordinates Sx, Sy and Sz of the diseased part S are calculated from the following formula.

$Sx=(1-h/H) \cdot X1$ $Sy=(1-h/H) \cdot Y1$ $Sz=h$ (4) A parallel displacement amount of the medical treatment base 1 is calculated from the difference between a desirable position of the patient 5 and the position (Sx, Sy, Sz) of the diseased part S.

When the above-mentioned arithmetic processings are terminated, the medical treatment base 1 is moved in parallel with horizontal and vertical directions by the medical treatment base controller 11 on the basis of commands of the electronic computer 10 until the desirable position. Thus, the position of the diseased part S of the patient 5 can be aligned with a predetermined three-dimensional coordinate position.

In the conventional moving body pursuit irradiating device mentioned above, when the three-dimensional coordinates are calculated, it is necessary to move the X-ray TV camera input device (an X-ray fluoroscope) every time. A position of the three-dimensional coordinates which is to be calculated must be also manually commanded every time. Further, a problem exists in that the calculation of the three-dimensional coordinates depends on mechanical accuracy of attachment of the X-ray TV camera input device and an absolute position of the patient. Therefore, it was difficult to obtain the three-dimensional coordinates in real time.

SUMMARY OF THE INVENTION

The present invention has been made to solve the above-mentioned problems, and an object of the present invention is to obtain a moving body pursuit irradiating device capable of automatically calculating the position of a tumor moving round within a leading body portion in real time, and securing a substantial required accuracy irrespective of the absolute accuracy of a mechanical system, and obtain a positioning method using this moving body pursuit irradiating device.

Another object of the present invention is to obtain a moving body pursuit irradiating device capable of selectively accurately irradiating a large dose of beam and reducing exposure to a normal tissue, and obtain a positioning method using this moving body pursuit irradiating device.

In this invention, there is provided a moving body pursuit irradiating device comprising: a linac for irradiating a medical treatment beam to a tumor; a tumor marker buried in the vicinity of the tumor; a first X-ray fluoroscope for picking up an image of the tumor marker from a first direction; a second X-ray fluoroscope for picking up the image of the tumor marker from a second direction at the same time as the first X-ray fluoroscope; first and second image input sections for digitizing first and second fluoroscopic images outputted from the first and second X-ray fluoroscopes; first and second recognition processing sections which execute template matching at a real time level at a predetermined frame rate by a shading normalization mutual correlation method for applying a template image of the tumor marker registered in advance to image information digitized by the first and second image input sections, and calculate first and second two-dimensional coordinates of the tumor marker; a central arithmetic processing section for calculating three-dimensional coordinates of the tumor marker from the first and second two-dimensional coordinates calculated by the first and second recognition processing sections; and an irradiating control section for controlling the irradiation of the medical treatment beam of the linac by the calculated three-dimensional coordinates of the tumor marker.

In the moving body pursuit irradiating device according to this invention, each of the first and second X-ray fluoroscopes intermittently picks up the image of the tumor marker when it is known that a moving speed of the tumor is low.

In the moving body pursuit irradiating device according to this invention, each of the first and second recognition processing sections limits an input image area for embodying the template matching when a maximum speed of the tumor marker can be estimated.

In the moving body pursuit irradiating device according to this invention, the central arithmetic processing section calculates a moving speed of the tumor marker from the three-dimensional coordinates of a fluoroscopic image just inputted and the position displacement of a fluoroscopic image in input timing previously set once, and adds a moving amount multiplied by a delay time provided by a series of processings to a recognizing coordinate of the present frame as a position correcting amount.

In the moving body pursuit irradiating device according to this invention, the central arithmetic processing section calculates a moving acceleration of the tumor marker from the three-dimensional coordinates of a fluoroscopic image just inputted and the position displacement of a fluoroscopic image in each of input timings previously set once and twice, and adds a position correcting amount corresponding to a delay time provided by a series of processings to a recognizing coordinate of the present frame.

The moving body pursuit irradiating device according to this invention further comprises a medical treatment base position control section for controlling the position of a medical treatment base such that this position of the medical treatment base is moved by performing an inverse operation from a moving amount of the tumor marker on the medical treatment base.

The moving body pursuit irradiating device according to this invention further comprises a multi-leaf collimator control section for dynamically controlling an irradiating field by opening and closing a multi-leaf collimator arranged in the linac by performing an inverse operation from a moving amount of the tumor marker.

In the moving body pursuit irradiating device according to this invention, a plurality of the tumor markers are included.

In the moving body pursuit irradiating device according to this invention, the central arithmetic processing section performs a control operation such that the X-ray of each of the first and second X-ray fluoroscopes is irradiated in a pulse shape by a trigger control section in synchronization with the predetermined frame rate, and no medical treatment beam of the linac is irradiated in irradiating timing of each of the first and second X-ray fluoroscopes.

In the moving body pursuit irradiating device according to this invention, the tumor marker has a surface color having a high absorbing property with respect to a visible ray and is stuck to the surface of a head portion instead of burying of the tumor marker in the vicinity of the tumor, and first and second TV cameras using a visible ray are used instead of the first and second X-ray fluoroscopes.

In the moving body pursuit irradiating device according to this invention, the central arithmetic processing section calculates a frequency distribution of the three-dimensional coordinates of the tumor marker by performing a monitoring operation for a predetermined time before a medical treatment is taken, and controls an operation of the irradiating control section such that a high frequency area is set to a medical treatment portion.

The moving body pursuit irradiating device according to this invention further comprises a third X-ray fluoroscope for picking up the image of the tumor marker from a third direction is arranged, and the central arithmetic processing section selectively uses two uninterfering X-ray fluoroscopes among the first, second and third X-ray fluoroscopes on the basis of an obtained gantry angle.

According to this invention, a positioning method using a moving body pursuit irradiating device comprises the steps of obtaining first and second fluoroscopic images by simultaneously picking up the image of a tumor marker buried in the vicinity of a tumor from first and second directions; executing template matching at a real time level at a predetermined frame rate by a shading normalization mutual correlation method for applying a template image of the tumor marker registered in advance to first and second digitized fluoroscopic images, and calculating first and second two-dimensional coordinates of the tumor marker on the basis of first and second fluoroscopic transformation matrices; calculating three-dimensional coordinates of the tumor maker on the basis of the first and second calculated two-dimensional coordinates; and positioning the medical treatment beam of a linac on the basis of the calculated three-dimensional coordinates of the tumor marker.

According to this invention, the positioning method using the moving body pursuit irradiating device further comprises the steps of: obtaining third and fourth fluoroscopic images by simultaneously picking up the image of a spatial coordinate calibrator arranged at an isocenter from the first and second directions in advance; and calculating the first and second fluoroscopic transformation matrices in advance by commands of six vertexes of the spatial coordinate calibrator displayed on the third and fourth fluoroscopic images.

BRIEF DESCRIPTION OF THE DRAWINGS

In the accompanying drawings:

FIG. 2A1–2C2 are views showing a fluoroscopic image of the moving body pursuit irradiating device in accordance with the embodiment 1 of this invention;

FIG. 7A–7C are views showing a fluoroscopic image in a case in which no tumor marker of the moving body pursuit irradiating device in accordance with the embodiment 1 of this invention is formed in a spherical shape;

FIG. 8 is a view showing a case in which the arrangement of a fluoroscope of the moving body pursuit irradiating device in accordance with the embodiment 1 of this invention is different;

FIG. 10 is a view showing an interlock of the moving body pursuit irradiating device in accordance with the embodiment 1 of this invention;

FIG. 15A–15C are timing charts showing a control of a frame rate in a moving body pursuit irradiating device in accordance with an embodiment 2 of this invention;

DESCRIPTION OF THE PREFERRED EMBODIMENTS

Embodiment 1

Figure 1:
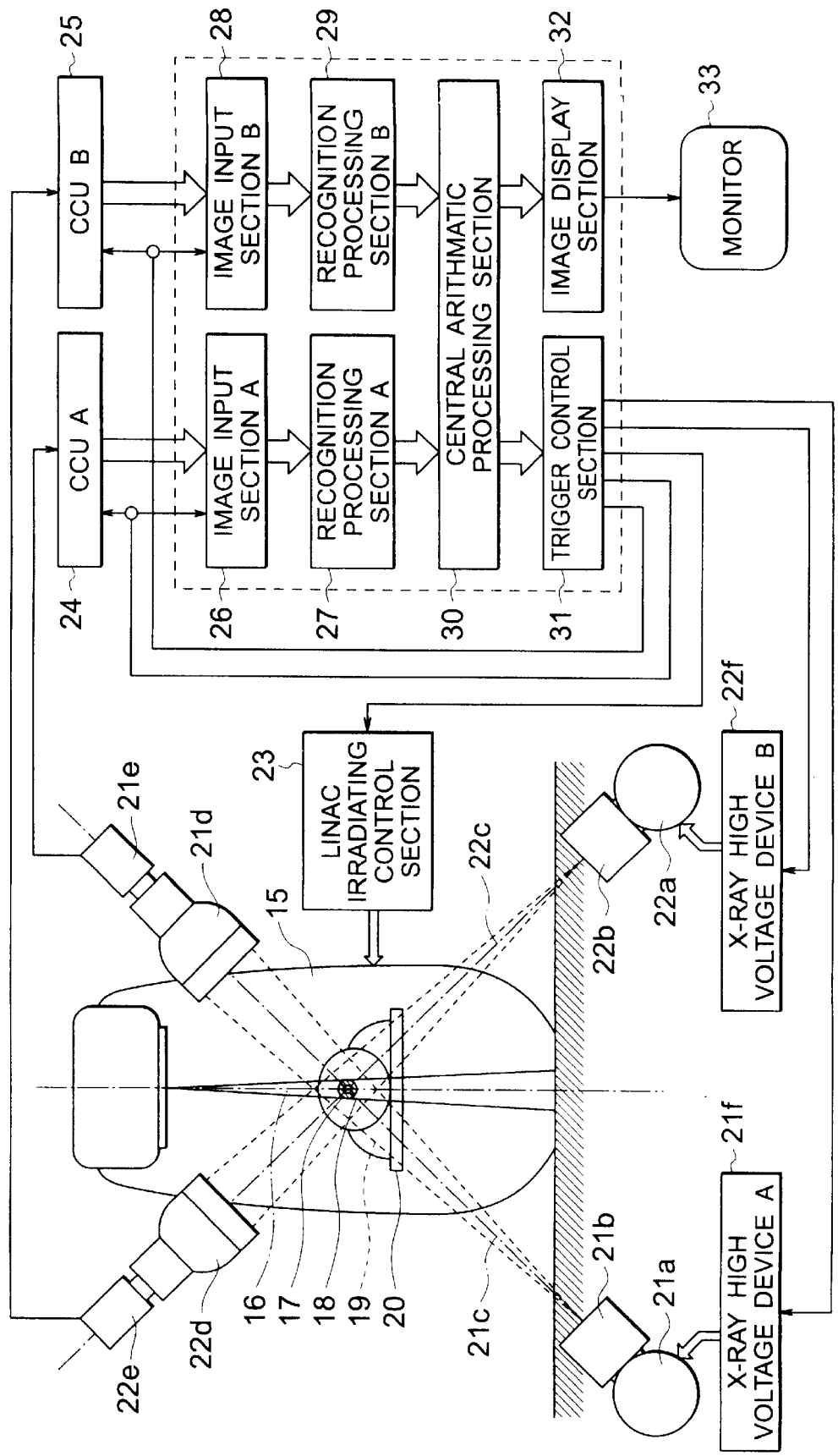
FIG. 1 is a block diagram showing the construction of a moving body pursuit irradiating device in accordance with an embodiment 1 of this invention.

A moving body pursuit irradiating device in accordance with an embodiment 1 of this invention will be next described with reference to the drawings. FIG. 1 is a view partially showing the construction of the moving body pursuit irradiating device in accordance with the embodiment 1 of this invention by blocks. In this figure, the same reference numerals as the conventional moving body pursuit irradiating device designate the same portions or corresponding portions.

In FIG. 1, reference numerals 15 and 16 respectively designate a linac and a medical treatment beam irradiated by this linac 15. Reference numeral 17 designates a tumor marker buried into a tumor within a patient's body and formed in a spherical shape and constructed by a material in which harm is small in a human body and the absorption of an X-ray is large. This material is constructed by Au, Pt, Ir, etc. having about 1 to 2 mm in diameter. Reference numerals 18, 19 and 20 respectively designate a tumor within the body, the patient and a medical treatment base having a roof constructed by a material such as CFRP, etc. for reducing the absorption of an X-ray.

In FIG. 1, reference numerals 21a, 21b and 21c respectively designate an X-ray tube A arranged below the floor of a medical treatment room, a collimator A for diaphragming the X-ray irradiated from the X-ray tube A, and the X-ray A irradiated from the X-ray tube A. Reference numerals 21d, 21e and 21f respectively designate an image intensifier A arranged in a ceiling of the medical treatment room at an opposite angle of this X-ray tube A through an isocenter, a TV camera A connected to the image intensifier A, and an X-ray high voltage device A for controlling an operation of the X-ray tube A. An X-ray fluoroscope A(21) is constructed by members from the above X-ray tube A(21a) to the x-ray high voltage device A(21f).

In this figure, reference numerals 22a, 22b and 22c respectively designate an X-ray tube B arranged below the floor of the medical treatment room, a collimator B for diaphragming the X-ray irradiated from the X-ray tube B, and the X-ray B irradiated from the X-ray tube B. Reference numerals 22d, 22e and 22f respectively designate an image intensifier B arranged in the ceiling of the medical treatment room at an opposite angle of this X-ray tube B through the isocenter, a TV camera B connected to the image intensifier B, and an X-ray high voltage device B for controlling an operation of the X-ray tube B. An X-ray fluoroscope B(22) is constructed by members from the above X-ray tube B(22a) to the X-ray high voltage device B(22f).

Further, in this figure, reference numerals 23, 24 and 25 respectively designate a linac irradiating control section for directly controlling on/off of a medical treatment beam of the linac 15, a cameral control unit (CCU) A, and a camera control unit (CCU)B. Reference numerals 26, 27 and 28 respectively designate an image input section A, a recognition processing section A, and an image input section B. Reference numerals 29, 30, 31, 32 and 33 respectively designate a recognition processing section B, a central arithmetic processing section, a trigger control section, an image display section and a monitor.

An operation of the moving body pursuit irradiating device in accordance with the above embodiment 1 will be next explained with reference to the drawings.

First, an X-ray irradiation allowing signal is applied from the trigger control section 31 to the X-ray high voltage devices A(21f) and B(22f) on the basis of commands of the central arithmetic processing section 30 so that an X-ray is irradiated from the X-ray tubes A(21a) and B(22a). Simultaneously, a synchronous signal is sent from the trigger control section 31 to the camera control units A(24) and B(25) and the image input sections A(26) and B(28). Images of the TV cameras A(21e) and B(22e) are sent to the recognition processing sections A(27) and B(29) while these images are synchronized with each other in a constant period.

The X-ray irradiated from the X-ray tube A passes through a portion near the tumor marker 17 buried in the vicinity of the tumor 18 within the body of the patient 19 on the CFRP medical treatment base 20. The X-ray then forms a fluoroscopic image A (see FIG. 2(a1)) on a tube face of the image intensifier A(21d). The fluoroscopic image A is converted to an electric signal by the TV camera A and is inputted to the image input section A through the camera control unit A. The fluoroscopic image A is then digitized to resolution of about 1024×1024 and gradation of about 256 stages per one pixel (see FIG. 2(b1)) and is sent to the recognition processing section A.

In this recognition processing section A, template matching is executed by a mutual correlation of shading normalization between a template image A (see FIG. 2(c1)) as a reference image of the tumor marker 17 stored in advance and the digitized fluoroscopic image A (see FIG. 2(b1)). A tumor marker coordinate A having a highest correlation degree on the digitized fluoroscopic image A is calculated and is sent to the central arithmetic processing section 30.

Similarly, the X-ray irradiated from the X-ray tube B passes through a portion near the tumor marker 17 buried in the vicinity of the tumor 18 within the body of the patient 19 on the medical treatment base 20. The X-ray then forms a fluoroscopic image B (see FIG. 2(a2)) on a tube face of the image intensifier B. The fluoroscopic image B is converted to an electric signal by the TV camera B and is inputted to the image input section B through the camera control unit B. The fluoroscopic image is then digitized to resolution of about 1024–1024 and gradation of about 256 stages per one pixel (see FIG. 2(b2)) and is sent to the recognition processing section B.

In this recognition processing section B, template matching is executed by a mutual correlation of shading normalization between a template image B (see FIG. 2(c2)) as a reference image of the tumor marker 17 stored in advance and the digitized fluoroscopic image B (see FIG. 2(b2)). A tumor marker coordinate B having a highest correlation degree on the digitized fluoroscopic image B is calculated and is sent to the central arithmetic processing section 30.

In a template matching method using the shading normalization mutual correlation, the following calculation is made between a reference image (template) registered-in advance and an image in which (it is considered that) a marker exists. An existing degree of the marker within an inspecting image is calculated by this calculation.

$$Q_{x,y} = \frac{\sum_{i,j}^{n} F_{x+i,y+j} G_{i,j} - n\overline{FG}}{\sqrt{\sum_{i,j}^{n} F_{x+i,y+j}^2 - n\overline{F}^2} \sqrt{\sum_{i,j}^{n} G_{i,j}^2 - n\overline{G}^2}}$$

In the actual calculation, a correlation value Qx,y of a template image Gi and a search image (a digitized fluoroscopic image) Fi is calculated while a local area Sx,y of the same size as a template beginning from (x,y) is sequentially shifted. It is then judged by the obtained correlation value whether or not an object equal to the template exists at coordinates (x,y).

The tumor marker 17 is constructed by a substance such as Au, Pt, Ir, etc. harmless in a human body and opaque with respect to the X-ray. Accordingly, it is possible to obtain a high discriminating property even in a complicated fluoroscopic image provided by internal organs and bones, etc. The tumor marker 17 is formed in a spherical shape having 1 to 2 mm in diameter. Accordingly, there are effects in which the tumor marker 17 is recorded in a spherical shape on the fluoroscopic image even when the tumor marker 17 is arranged in any way within the body and a fluoroscopic operation is performed in any direction. Accordingly, it is very effective to reduce a processing speed since perfect effects can be obtained in one trial in contrast to a general template matching method in which trials for plural templates according to various angles are sequentially made and a highest recognizing degree is obtained when the shape of a recognized object is changed by rotation, etc. within a search image.

In the central arithmetic processing section 30, the tumor marker coordinate A is converted to an equation of a straight line by a fluoroscopic transformation matrix $M_A$ of a fluoroscopic system A stored in advance. In this equation, it is considered that the tumor marker 17 exists near the isocenter thereabove.

In the central arithmetic processing section 30, the tumor marker coordinate B is similarly converted to an equation of a straight line by a fluoroscopic transformation matrix $M_B$ of a fluoroscopic system B stored in advance. In this formula, it is considered that the tumor marker 17 exists near the isocenter thereabove.

Further, the central arithmetic processing section 30 obtains three-dimensional coordinates of the tumor marker 17 by calculating an intersecting point of these two equations of straight lines obtained in this way.

When the obtained three-dimensional coordinates lie within a predetermined range, the central arithmetic processing section 30 sends a medical treatment beam enable signal to the linac irradiating control section 23. The linac irradiating control section 23 gives commands for irradiating the medical treatment beam 16 to the linac 15.

Conversely, when no obtained three-dimensional coordinates of the tumor marker 17 lie within the predetermined allowing range, no medical treatment beam enable signal is sent to the linac irradiating control section 23, and the linac irradiating control section 23 gives commands for interrupting the medical treatment beam irradiation to the linac 15. Thus, the medical treatment beam 16 is irradiated by the linac 15 only when the tumor marker 17 lies within the predetermined allowing range.

The fluoroscopic transformation matrix M required in the central arithmetic processing section 30 is calculated as follows. FIG. 3 is a view showing a spatial coordinate calibrator 40 used in the moving body pursuit irradiating device in accordance with this embodiment 1.

Figure 3A:
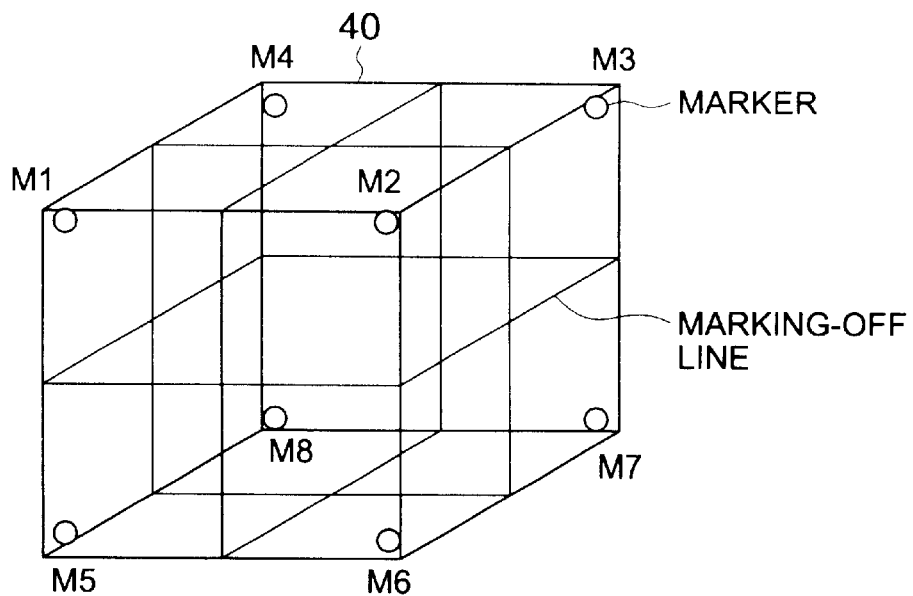
FIG. 3A–3B are views showing a spatial coordinate calibrator used in a positioning method using the moving body pursuit irradiating device in accordance with the embodiment 1 of this invention.
Figure 3B:
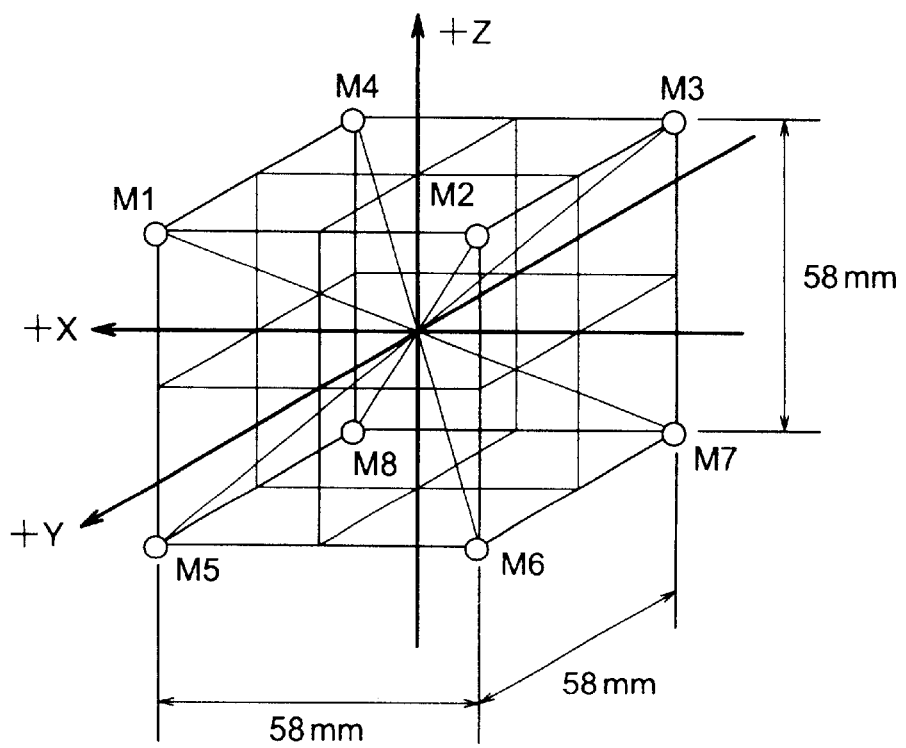
Figure 4A:
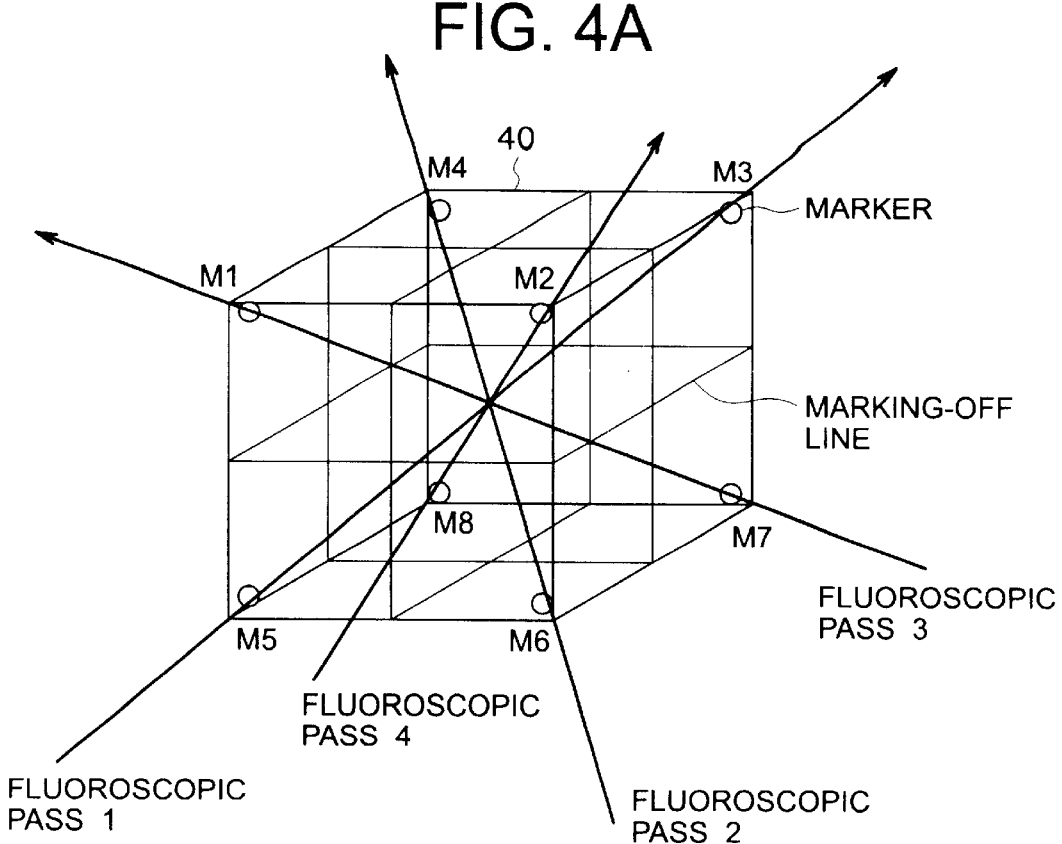
FIG. 4A–4E are views showing fluoroscopic passes of the spatial coordinate calibrator used in the positioning method using the moving body pursuit irradiating device in accordance with the embodiment 1 of this invention.
Figure 4B:
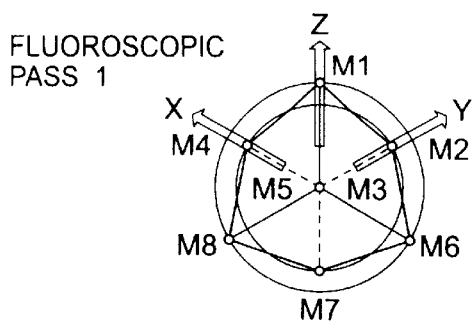
Figure 4C:
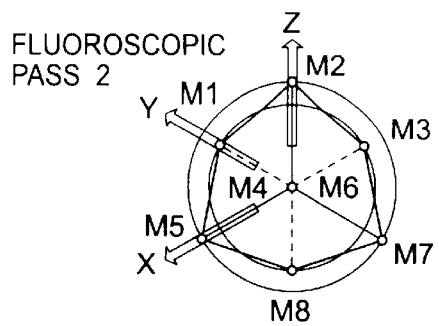
Figure 4D:
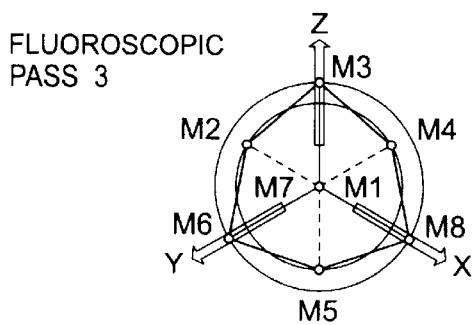
Figure 4E:
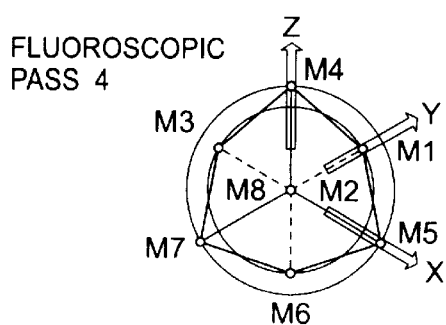

As shown in FIG. 3(a), in this spatial coordinate calibrator 40, a cube is constructed by a relatively transparent material such as acrylic, etc. with respect to the X-ray and approximately has a one side length from 40 to 80 mm. Spherical substances (markers) M1 to M8 such as Au, W, Pb, etc. approximately having a diameter from 1 to 2 mm and opaque with respect to the X-ray are precisely buried near vertexes of the cube so as to be located in constant positions from the respective vertexes. Further, marking-off lines are made between middle points of opposite sides on respective cubic faces.

FIG. 4 is a view showing fluoroscopic passes in which the X-ray passes through the spatial coordinate calibrator 40 by the fluoroscope. In this figure, for example, FIG. 4(b) shows a fluoroscopic image of the spatial coordinate calibrator 40 in a state in which a fluoroscopic pass 1 passing from a mark M5 of the spatial coordinate calibrator 40 to a mark M3 is set to a center. Similarly, FIGS. 4(c) to 4(e) show fluoroscopic passes 2 to 4.

First, the spatial coordinate calibrator 40 is arranged on the medical treatment base 20 and is aligned with the medical treatment base 20 in position along guides of the marking-off lines described on the respective faces of the spatial coordinate calibrator 40 such that a center of the spatial coordinate calibrator 40 is equal to an isocenter by using a laser pointer used in positioning of the medical treatment.

Next, an X-ray irradiation allowing signal is applied from the trigger control section 31 to the X-ray high voltage device A by commands of the central arithmetic processing section 30. Thus, the X-ray is irradiated from the X-ray tube A so that a fluoroscopic image A of the spatial coordinate calibrator 40 is formed on the image intensifier A.

The fluoroscopic image A is then converted to an electric signal by the TV camera A and is digitized by the image input section A through the camera control unit A. The digitized signal is inputted to the central arithmetic processing section 30 and is displayed in the monitor 33 by the image display section 32.

An operator gives commands to the central arithmetic processing section 30 such that the positions of fluoroscopic images at six vertexes among fluoroscopic images at eight vertexes (markers) of the spatial coordinate calibrator 40 displayed in the monitor 33 correspond to respective real coordinates from the isocenter.

The central arithmetic processing section 30 obtains coordinates $(x_{Ai}, y_{Ai})|i=1,6$ on a fluoroscopic image of the tumor marker 17 by designating positions on the fluoroscopic images, and also obtains three-dimensional coordinates $(X_{Ai}, Y_{Ai}, Z_{Ai})|i=1,6$ correspondingly provided with the isocenter as an origin. The central arithmetic processing section 30 also calculates a fluoroscopic transformation matrix $M_A$ in projective geometry in the fluoroscopic system A.

If a homogeneous coordinate with respect to the real coordinate in a three-dimensional space of the tumor marker 17 is set to $[a_A]$ and a homogeneous coordinate with respect to a coordinate on the fluoroscopic image of the tumor marker 17 is set to $[b_A]$, the fluoroscopic transformation matrix $M_A$ can be expressed as $[a_A M_A]=[b_A]$ by 4×3 and a matrix $M_A$ of rank 3. Combinational information of [a] and [b] at six points is required to generally calculate the matrix $M_A$. Therefore, six vertex coordinates of the spatial coordinate calibrator 40 are used.

Similarly, an X-ray irradiation allowing signal is applied from the trigger control section 31 to the X-ray high voltage device B by commands of the central arithmetic processing section 30. Thus, the X-ray is irradiated from the X-ray tube B so that a fluoroscopic image B of the spatial coordinate calibrator 40 is formed on the image intensifier B.

The fluoroscopic image B is then converted to an electric signal by the TV camera B and is digitized by the image input section B through the camera control unit B. The digitized signal is inputted to the central arithmetic processing section 30 and is displayed in the monitor 33 by the image display section 32.

An operator gives commands to the central arithmetic processing section 30 such that the positions of fluoroscopic images at six points among fluoroscopic images at eight vertexes (markers) of the spatial coordinate calibrator 40 displayed in the monitor 33 correspond to respective real coordinates from the isocenter.

The central arithmetic processing section 30 obtains coordinates $(x_{Bi}, y_{Bi})|i=1,6$ on a fluoroscopic image of the tumor marker 17 by designating positions on the fluoroscopic images, and also obtains three-dimensional coordinates $(X_{Bi}, Y_{Bi}, Z_{Bi})|i=1,6$ correspondingly provided with the isocenter as an origin. The central arithmetic processing section 30 also calculates a fluoroscopic transformation matrix $M_B$ in projective geometry in the fluoroscopic system B.

If a homogeneous coordinate with respect to the real coordinate in a three-dimensional space of the tumor marker 17 is set to $[a_B]$ and a homogeneous coordinate with respect to a coordinate on the fluoroscopic image of the tumor marker 17 is set to $[b_B]$, the fluoroscopic transformation matrix $M_B$ can be expressed as $[a_B M_B]=[b_B]$ by 4×3 and a matrix $M_B$ of rank 3.

When the fluoroscopic transformation matrix M is determined and coordinates at points on the fluoroscopic image are calculated, a coordinate group (an equation of a straight line) capable of making corresponding points exist within the three-dimensional space is calculated by the above transformation formula. Accordingly, two equations of straight lines each passing coordinates of the tumor marker within this space are obtained from the fluoroscopic images A and B obtained by looking at one tumor marker 17 by fluoroscopy by the fluoroscopic systems A and B. Three-dimensional coordinates of the tumor marker 17 can be calculated by calculating an intersecting point of these straight lines.

Application of Separate Recognizing Algorithm

In the above explanation, the recognition processing sections A and B (27 and 29) use the template matching method by the shading normalization mutual correlation as a calculating algorithm of two-dimensional coordinates of the tumor marker 17 on the fluoroscopic image. However, there is a case in which it is also sufficient to use a template matching method using a binary image and an image lower in gradation number in accordance with the state of a detected body in the calculating algorithm of the two-dimensional coordinates. In this case, processings of the recognition processing sections A and B are greatly simplified.

Three-dimensional Coordinate Calculating Method

Figure 5:
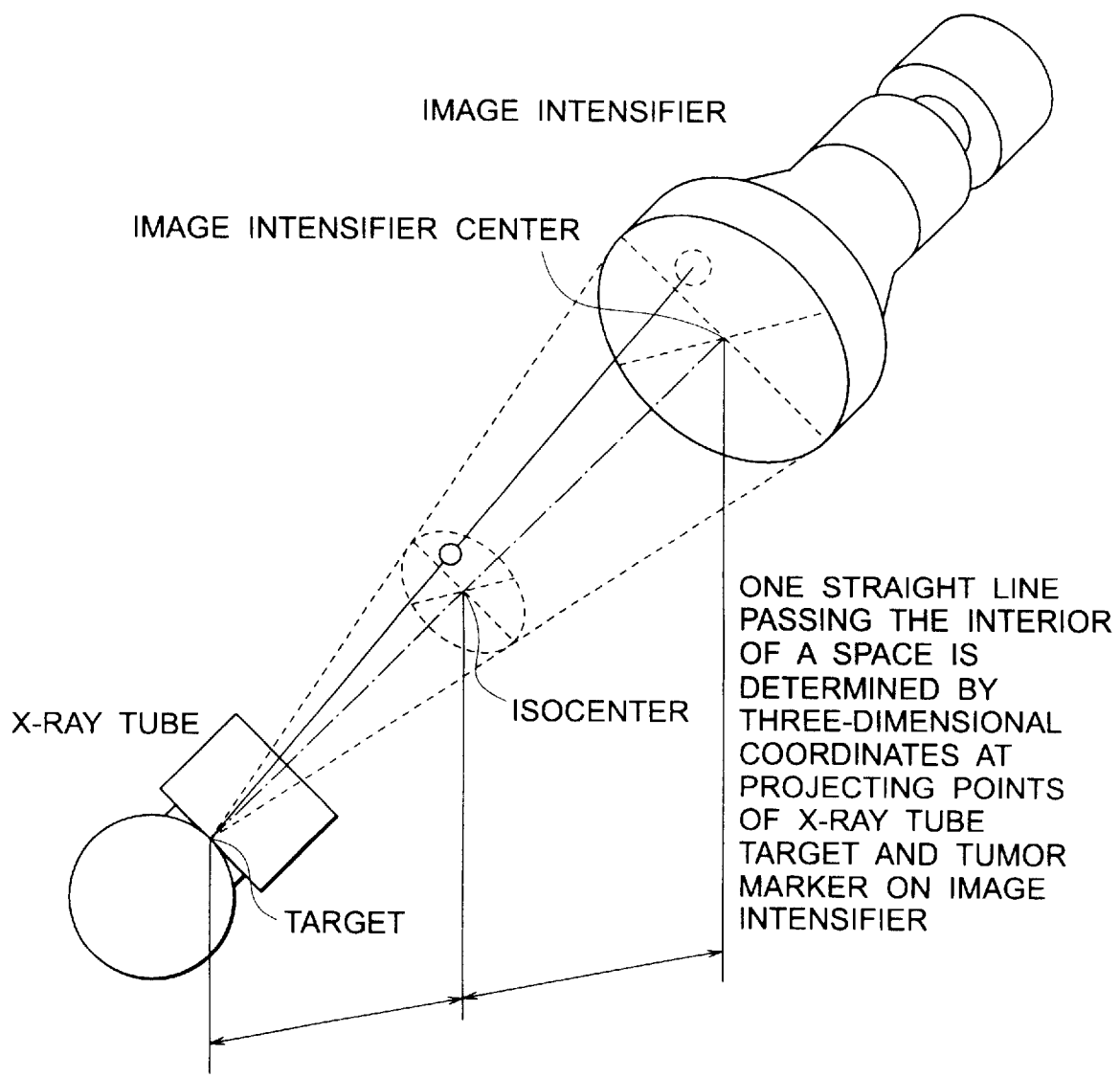
FIG. 5 is a view showing a three-dimensional coordinate calculating method of the moving body pursuit irradiating device in accordance with the embodiment 1 of this invention.

In the above explanation, the central arithmetic processing section 30 uses the spatial coordinate calibrator 40 as a method for calculating three-dimensional coordinates, and the three-dimensional coordinates are calculated by calculating the fluoroscopic transformation matrix in advance by projective geometry. However, if mechanical accuracies of the fluoroscope and the linac are respectively held at high levels, the three-dimensional coordinates can be also calculated by a trigonometric survey technique as shown in FIG. 5. In this case, no spatial coordinate calibrator 40 is required and an operation for picking up an image of the spatial coordinate calibrator 40 and an operation for calculating the fluoroscopic transformation matrix are not required. Accordingly, it is also possible to remove a complicated matrix calculation in processing for calculating the three-dimensional coordinates.

Shape of Spatial Coordinate Calibrator

Figure 6A:
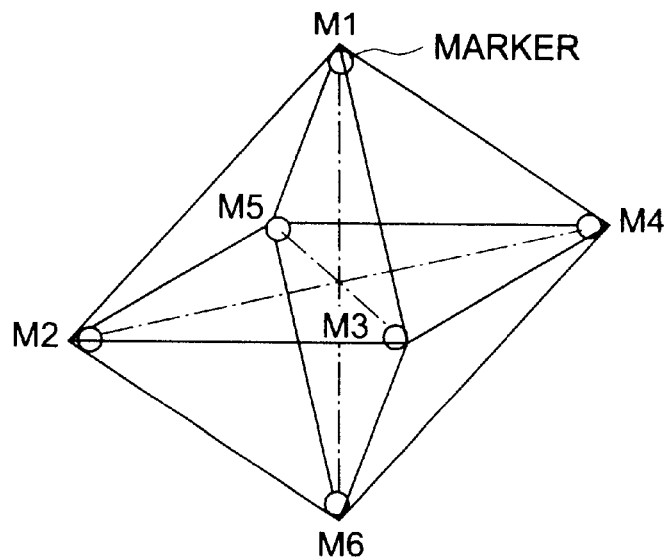
FIG. 6A–6B are views showing another shape of the spatial coordinate calibrator used in the positioning method using the moving body pursuit irradiating device in accordance with the embodiment 1 of this invention.
Figure 6B:
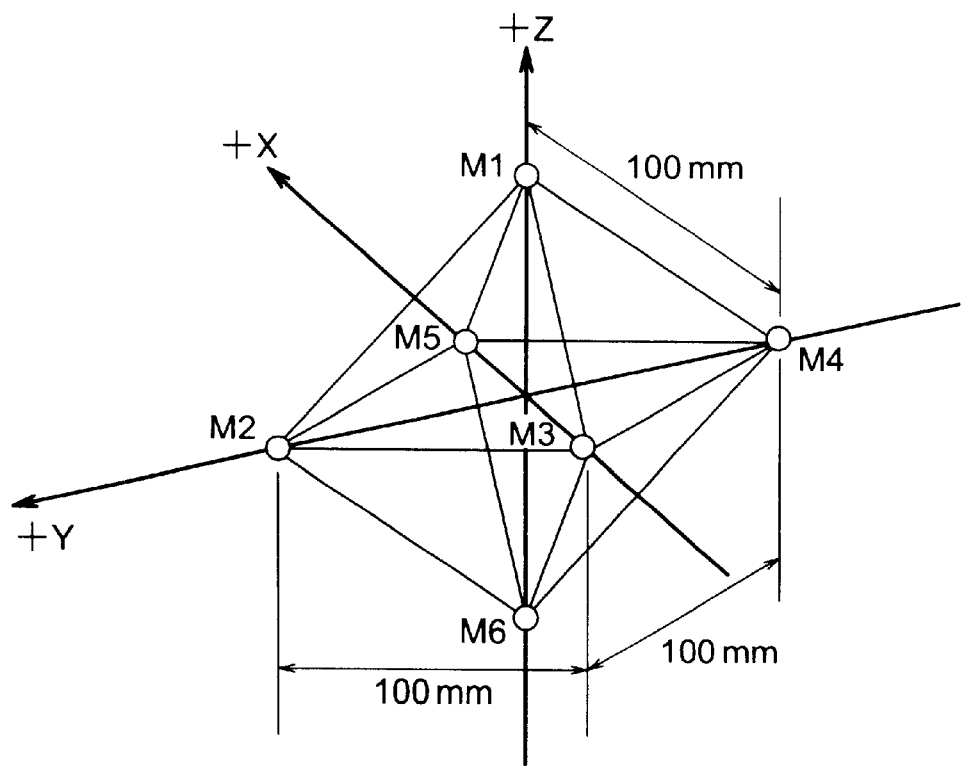
Figure 9A:
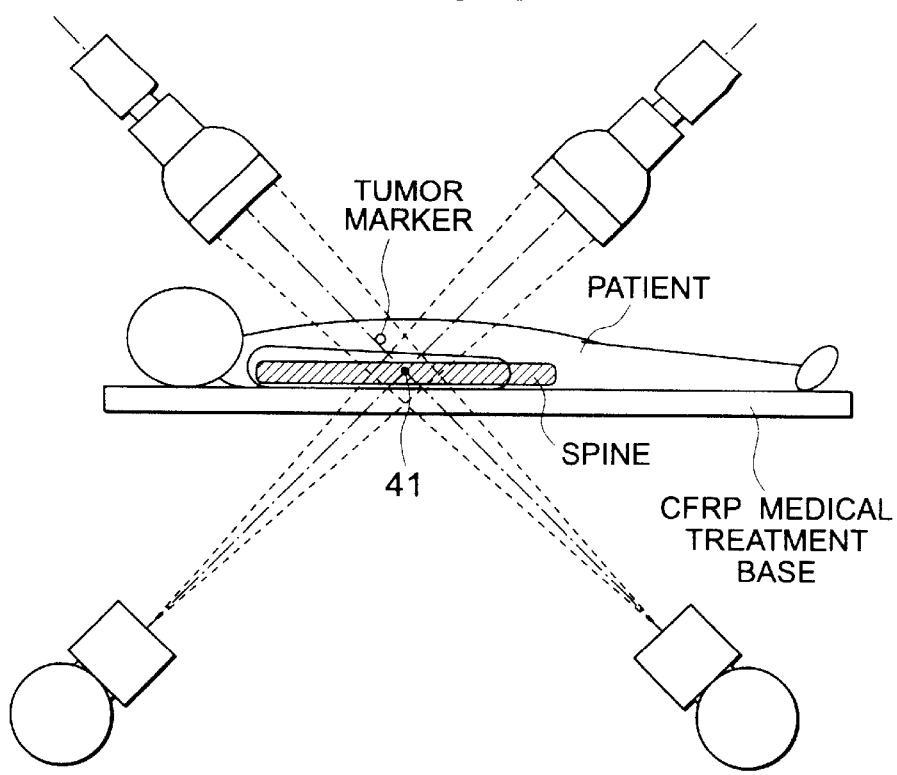
FIG. 9A–9B are views showing that the moving body pursuit irradiating device in accordance with the embodiment 1 of this invention is applied to the positioning of a land mark.
Figure 9B:
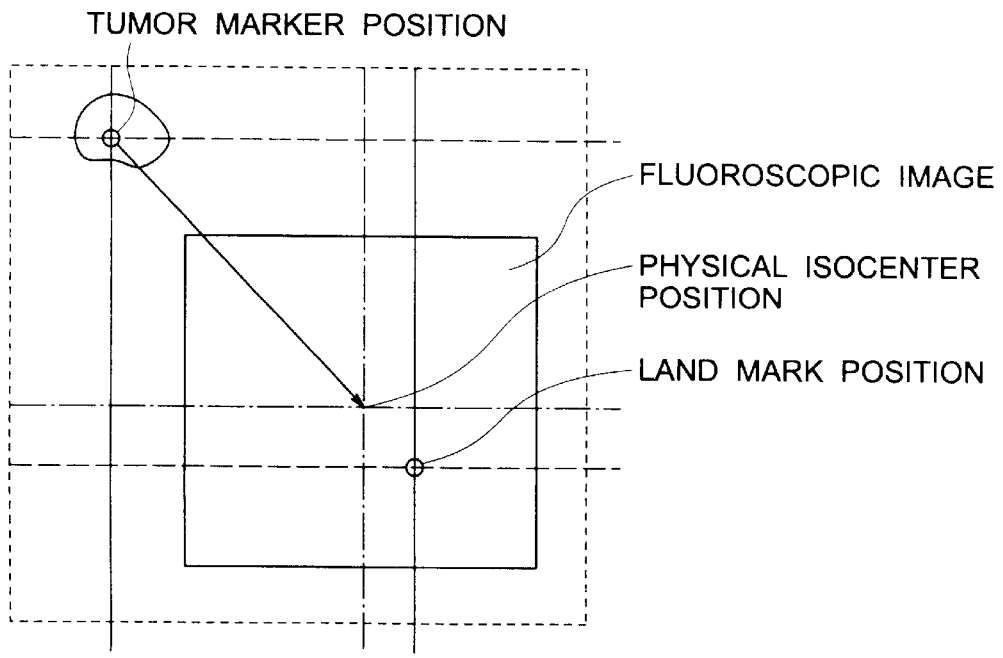

In the above explanation, the shape of the spatial coordinate calibrator 40 is set to a cubic shape. However, it is not necessary to particularly set the shape of the spatial coordinate calibrator 40 to a cubic shape except for simplicity of an operation and easiness in understanding. As shown in FIG. 6, it is needless to say that similar effects can be obtained even when the spatial coordinate calibrator is constructed by an object of a separate shape in which three-dimensional coordinates at six points within the space can correspond to two-dimensional coordinates at the six points obtained on a fluoroscopic image face by looking at these six points by fluoroscopy.

In FIG. 6, reference numerals M1 to M6 designate spherical bodies (markers) of Au, Pb, W. etc. having Ø2 mm and arranged at vertexes of a regular octahedron having 100 mm in one side length.

Case in which no Tumor Marker is Spherical

The above explanation is characterized in that the tumor marker buried in the vicinity of a tumor is spherical. However, a tumor marker formed in a bar shape, an elliptical shape, etc. may be also used. In this case, as shown in FIG. 7, plural templates are used at a template matching time and a template having a highest correlation degree is determined so that torsion and rotation of a tissue in the vicinity of the tumor marker can be detected. Accordingly, a tumor position can be also specified even when a movement of the tumor is not a simple parallel displacement with respect to a movement of the tumor marker but includes torsion and a rotating movement.

In FIG. 7(c), coordinates and an inclination of the tumor marker are obtained by searching plural template images registered in advance in the fluoroscopic image and providing a template image showing a highest correlation value.

Case in which arrangements of X-ray fluoroscope are different from each other

In the above explanation, two X-ray tubes are arranged below the floor and two corresponding image intensifiers are arranged in the ceiling. However, different arrangements of the X-ray tubes and the image intensifiers may be also used. For example, as shown in FIG. 8, two fluoroscopes of a moving type obtained by setting the X-ray tubes and the image intensifiers to a set may be also used. In this case, effects similar to those in the above explanation are obtained if the two fluoroscopes are suitably arranged in accordance with a tumor position and a position of the linac at a medical treatment time, and the fluoroscopic transformation matrix is calculated by the spatial coordinate calibrator every arrangement and a template image is reinputted.

Application to Positioning of Land Mark.

In the above explanation, the tumor marker 17 is used to detect the movement of a tumor. However, a patient can be precisely positioned by arranging a marker constructed by a material, a shape and a size equivalent to those of the tumor marker as a land mark in an immovable position within a body. Reference numeral 14 designates a land mark stuck to a bone (e.g., the spine) considered to be an immovable portion within the body or buried in this bone. The positional relation of the land mark 41 and a tumor portion is set to be determined at a planning time of the medical treatment. First, the patient is coarsely positioned such that the land mark 41 is imaged as a fluoroscopic image. Three-dimensional coordinates of the land mark 41 can be calculated from an image of the land mark on the fluoroscopic image by using two fluoroscopes. As mentioned above, the positional relation of the land mark position and the tumor is known. Accordingly, moving amounts of the medical treatment base in X, Y and Z directions can be immediately calculated to move the tumor to the isocenter. It is effective to precisely position the patient in comparison with a case in which a body surface marker too unstable to consider this marker as an immovable point is used.

With Respect to Interlock

In the above explanation, a beam enable signal is controlled such that the medical treatment beam 16 of the linac 15 is irradiated when the tumor marker 17 lies within a prescribed allowing range, and no medical treatment beam 16 is irradiated when the tumor marker 17 lies outside the allowing range. However, as shown in FIG. 10, the moving body pursuit irradiating device can be constructed such that an interlock signal for stopping the medical treatment beam 16 is outputted when a correlation degree value of two fluoroscopic images is lower than a prescribed threshold value in template matching results with respect to these two fluoroscopic images, or when it is judged that two straight lines to have tumor markers respectively obtained from the two fluoroscopic images exceed prescribed values in their distances and do not cross each other in an effective range. In this case, there is an effect for restraining a defective operation due to an error in recognition.

With Respect to User Interface

Figure 11A:
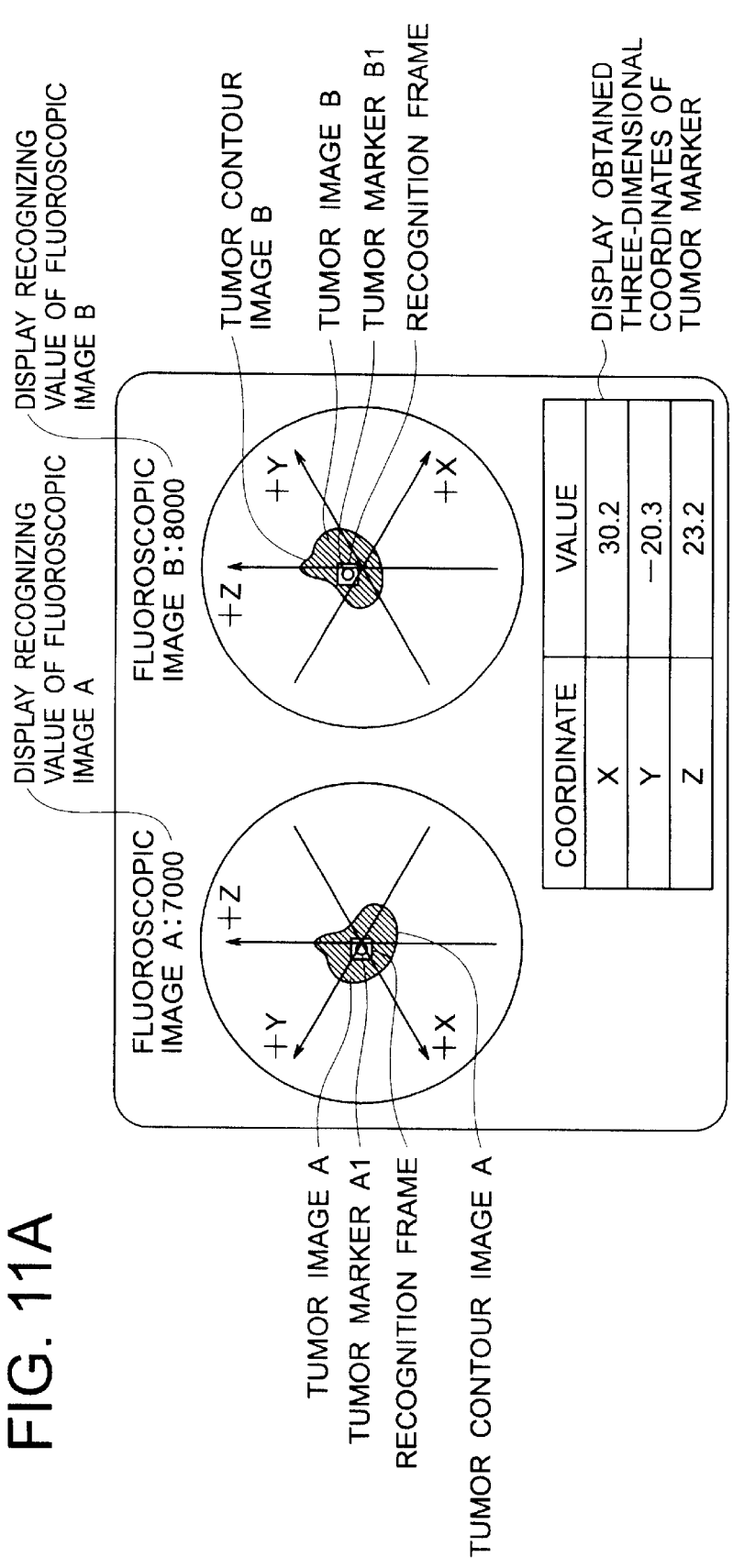
FIG. 11A–11B are views showing a user interface of the moving body pursuit irradiating device in accordance with the embodiment 1 of this invention.
Figure 11B:
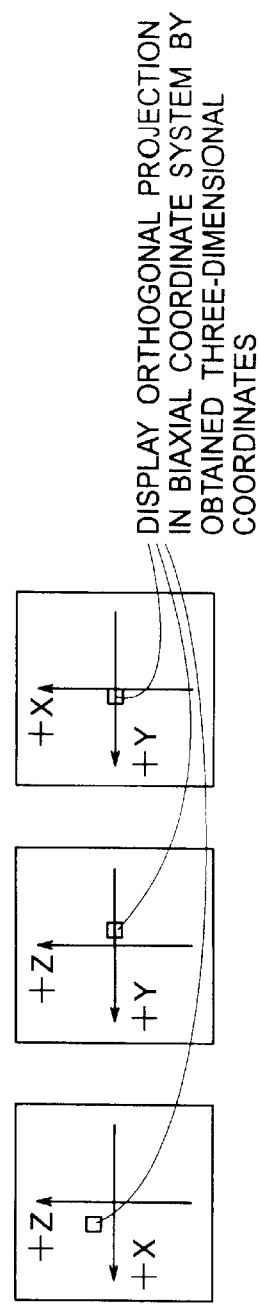

In the above explanation, video information inputted to the image input sections A and B is used only within the moving body pursuit irradiating device. However, there are effects in which an operator can visually grasp a recognizing situation of the tumor markers by sending the two inputted images and the recognizing situation to the image display section 32 and displaying these images and the recognizing situation in the monitor 33 in real time as shown in FIG. 11.

Application to Medical Treatment of Small Sealed Source

Figure 12A:
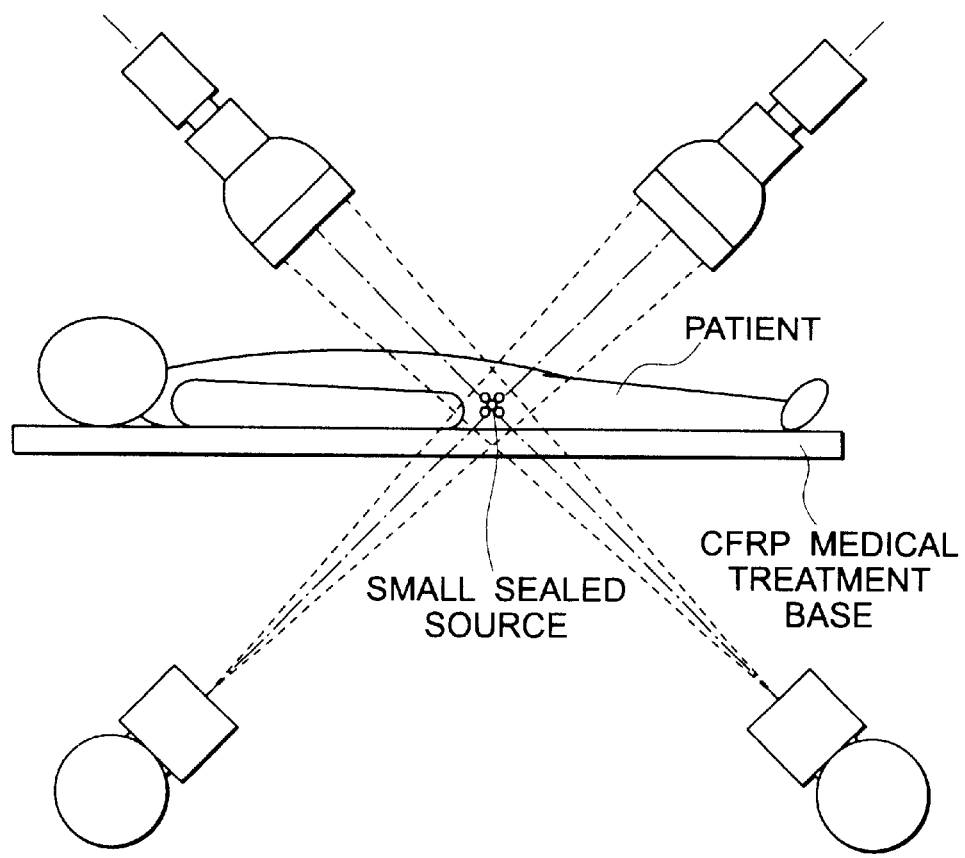
FIG. 12A–12B are views showing that the moving body pursuit irradiating device in accordance with the embodiment 1 of this invention is applied to the medical treatment of a small sealed source.
Figure 12B:
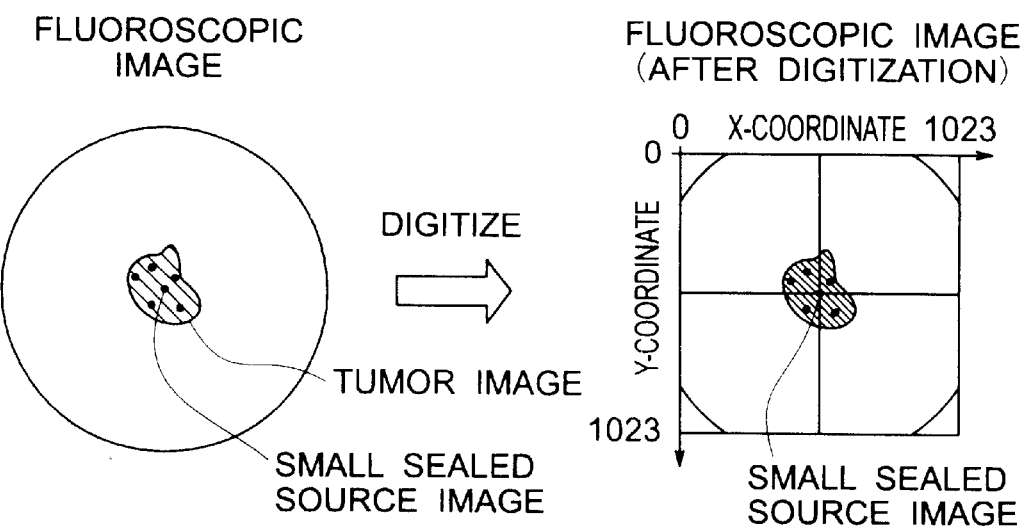

Further, in the above explanation, the present invention is applied to the moving body pursuit irradiating device. However, effects similar to those in the above embodiment 1 are obtained even when the present invention is applied to a radiation diagnostic device and a moving amount observing device. For example, as shown in FIG. 12, in the case of the medical treatment of a small sealed source for medically treating a cancer, etc. by inserting or sticking a radioisotope into a body, a three-dimensional position of the radioisotope can be instantly grasped when a form of this radioisotope is stored. If the positional relation of the tumor and a normal tissue around this tumor is grasped at a planning of the CT medical treatment, it is possible to grasp a dose distribution in consideration of a moving which was impossible so far.

Application to Catheter Operation within Body

Figure 13A:
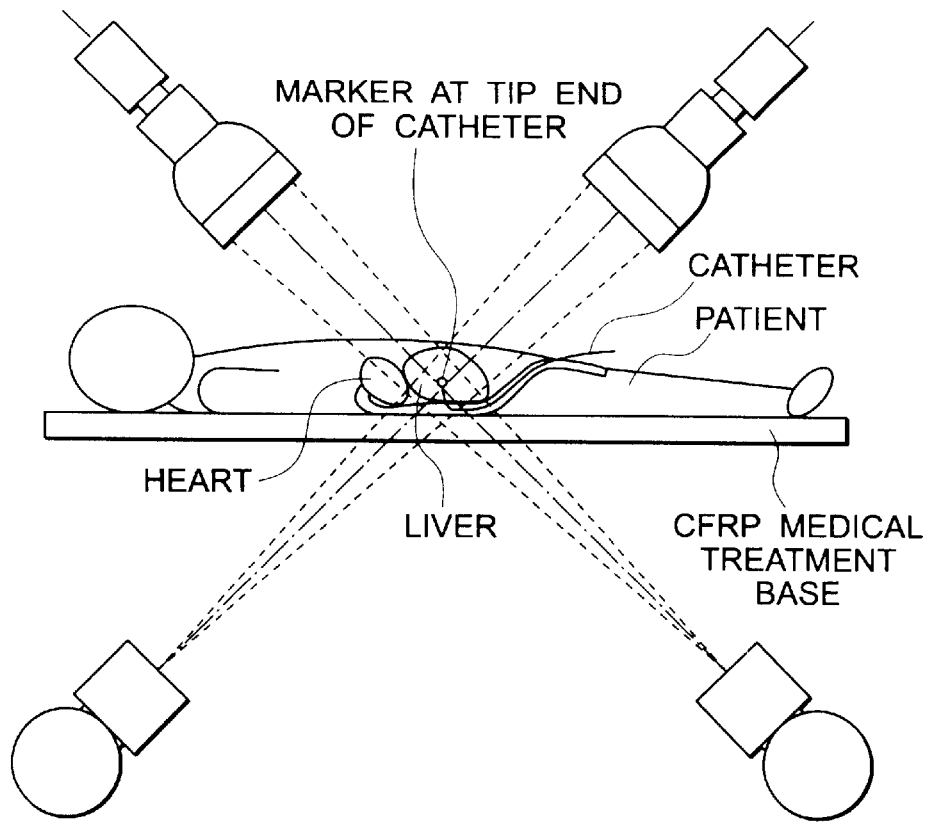
FIG. 13A–13B are views showing that the moving body pursuit irradiating device in accordance with the embodiment 1 of this invention is applied to a catheter operation within a body.
Figure 13B:
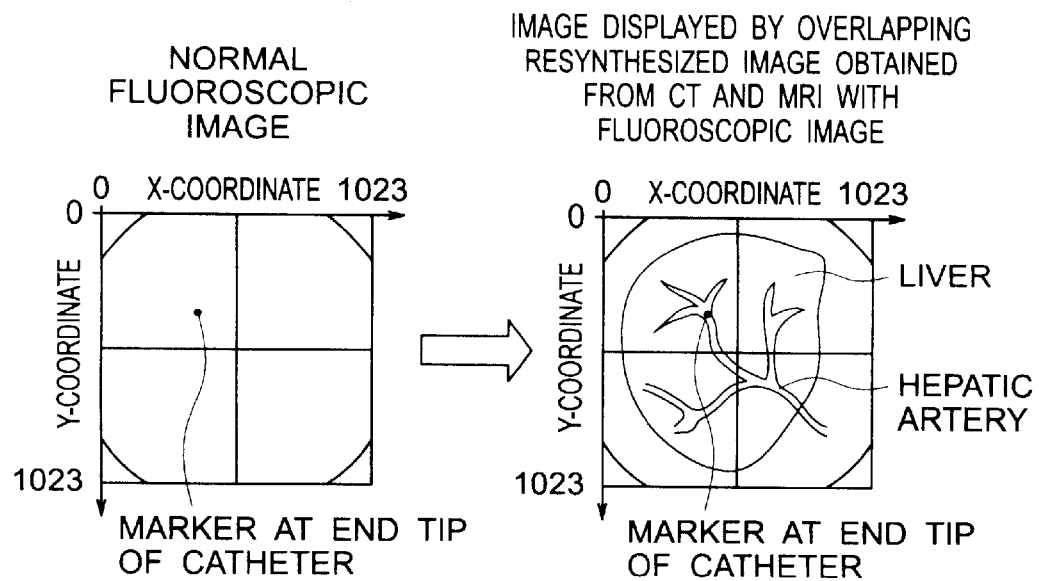

As shown in FIG. 13, when a metallic marker is attached to a tip end portion of each of a catheter and an endoscope in a thrombus dissolving technique (PTCA) of heart-coronary artery, brain-artery and a peripheral blood vessel, an operation of a pace maker, a general chest abdomen contrast such as a carotid embolic technique of a liver tumor, etc., operations within alimentary canal and bronchus, an operation within ureter via bladder, etc., a position of the catheter tip end and a morbid portion can be grasped in real time on the basis of CT data photographed in advance. When images of the endoscope within the blood vessel, etc. are again synthesized from a CT image and an advancing root of the catheter is planned in advance, this moving body pursuit irradiating device can be used as a navigator in real time. It takes useless time to operate the catheter since an operator operates the catheter while the operator imagines running of the blood vessel, etc. in the operator's head till now. However, in the present invention, the catheter operation is reliable and can be terminated for a short time so that exposure of the operator can be reduced and a remote control operation can be also performed.

Application to Navigator during Surgical Operation

Figure 14A:
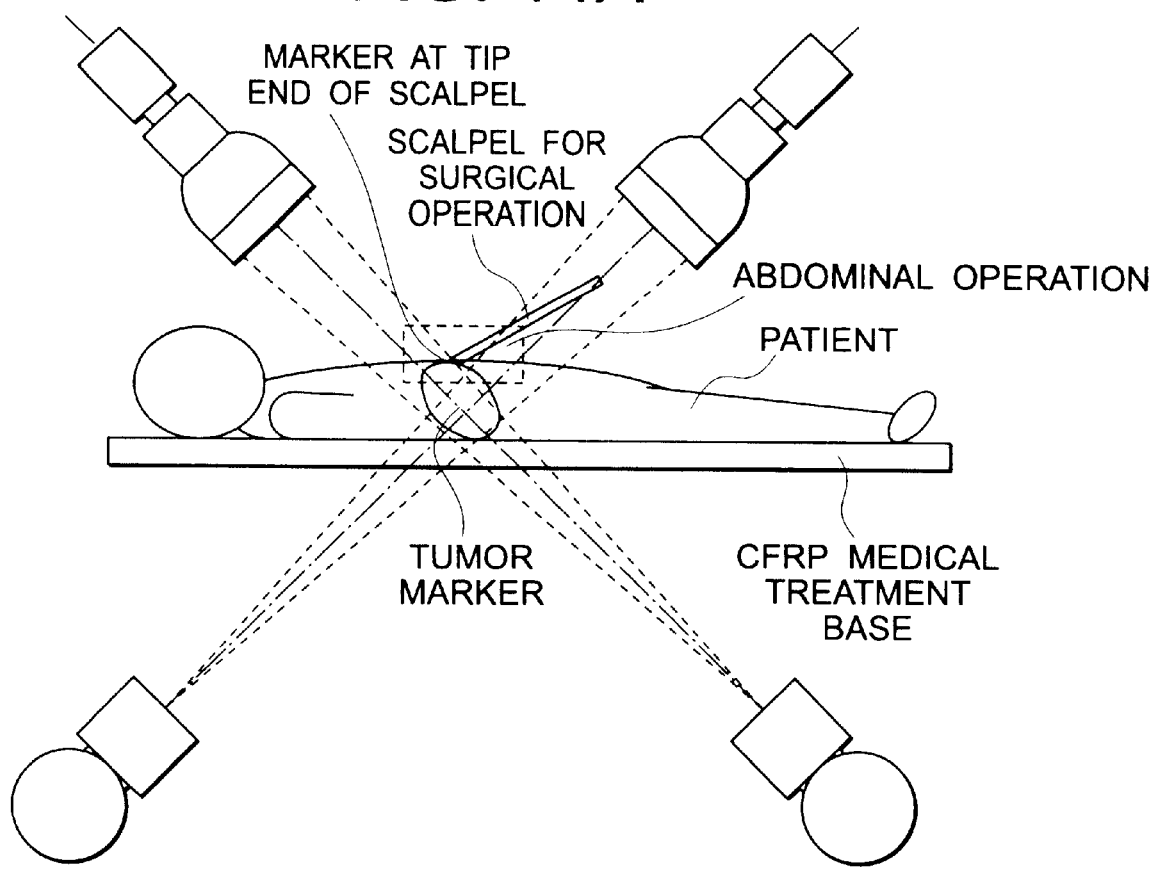
FIG. 14A–14B are views showing that the moving body pursuit irradiating device in accordance with the embodiment 1 of this invention is applied to a navigator during a surgical operation.
Figure 14B:
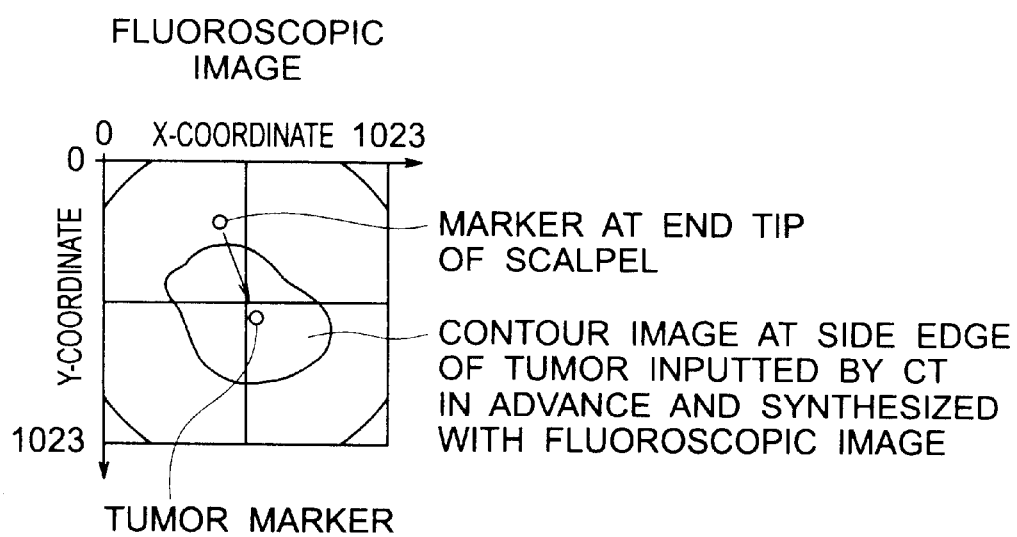

There have been reports till now with respect to a navigator for a surgical operation. However, in these reports, only the position of a tip end of each of a scalpel, a CUSA and the catheter is known and no coordinates of a tumor position itself can be grasped. Therefore, for example, when a medullary liquid is leaked in an instant of trephination in a brain operation and a CT photographing time and a brain position are changed, a fatal defect exists in that meaning of the navigator is lost. In this moving body pursuit irradiating device, as shown in FIG. 14, if a tumor marker is inserted in advance and is attached to a tip end of the scalpel, original navigation can be performed while the position of the tumor itself is grasped. Further, the navigation can be performed in real time even when a morbid portion is moving at any time. Accordingly, the moving body pursuit irradiating device functions as a navigator in any surgical operation of a leading body portion except for the brain.

Embodiment 2

(control of frame rate)

A moving body pursuit irradiating device in accordance with an embodiment 2 of this invention will be explained with reference to the drawings. FIG. 15 is a view showing the control of a frame rate of the moving body pursuit irradiating device in accordance with the embodiment 2 of this invention.

In the above embodiment 1, as shown in FIG. 15(a), a fluoroscopic image is inputted at a normal video rate of about 30 frame/second. However, when it is known that a moving speed of the tumor within the body is low, the fluoroscopic image can be intermittently inputted e.g., at video rates of 15 frame/second (see FIG. 15(b)) and 10 frame/second (see FIG. 15(c)) and the operation of the moving body pursuit irradiating device can be controlled such that no X-ray is irradiated from a fluoroscope except for a time at which the X-ray is required to input an image. In this case, an exposure amount of the X-ray due to the fluoroscope can be reduced.

Embodiment 3

(setting of search area)

Figure 16:
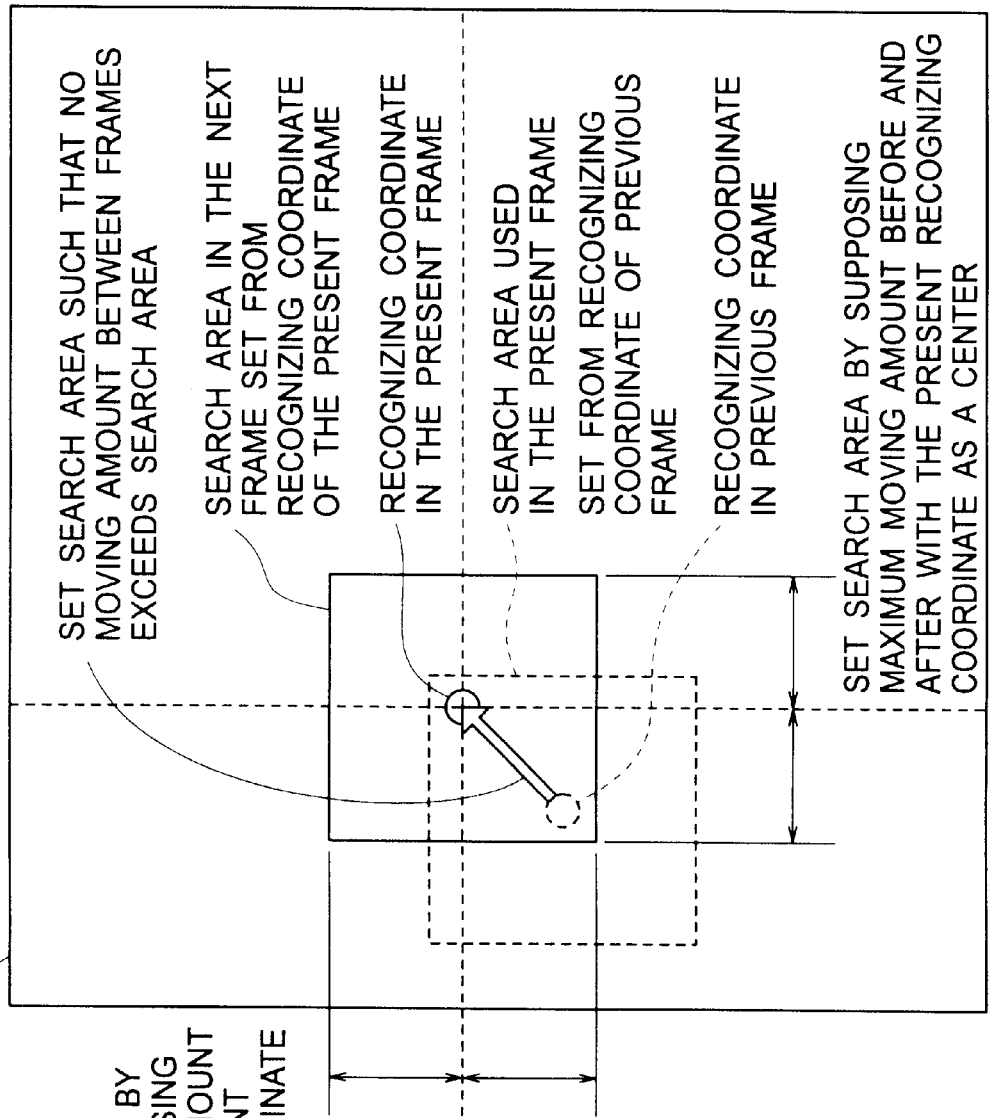
FIG. 16 is a view showing the setting of a search area in a moving body pursuit irradiating device in accordance with an embodiment 3 of this invention.

A moving body pursuit irradiating device in accordance with an embodiment 3 of this invention will be explained with reference to the drawings. FIG. 16 is a view showing the setting of a search area of the moving body pursuit irradiating device in accordance with the embodiment 3 of this invention.

In the above embodiment 1, image recognizing processing is performed by the template matching method with respect to all image areas digitized by the image input sections A and B. However, if it is noticed that the tumor marker 17 is moved at random but is continuously moved with respect to a time axis, an input image area for embodying template matching can be limited when a maximum speed of the tumor marker 17 can be estimated.

Namely, for example, the input image is digitized in a constant period of 30 frame/second. Accordingly, in this case, a maximum moving amount of the marker between an image inputted at a certain time and an image inputted in the next timing can be calculated by supposing that the tumor marker 17 is moved by $\frac{1}{30}$ second at a maximum speed.

Accordingly, as shown in FIG. 16, it is known that it is sufficient to execute the image recognizing processing using the template matching method with respect to an area in which maximum moving amounts of the marker between frames are added and subtracted in vertical, leftward and rightward directions in a state in which a coordinate of the tumor marker 17 obtained by an image previously inputted once is set to a center.

Thus, a useless arithmetic operation can be restrained by dynamically changing an area for performing the image recognizing processing every frame. Accordingly, there is an effect for restraining scales of H/W and S/W of the recognition processing sections A and B. Further, there is also an effect in which the image recognizing processing capable of following a higher speed movement of the tumor marker 17 can be realized in the recognition processing section having H/W of the same scale.

Embodiment 4

(position estimate)

Figure 17:
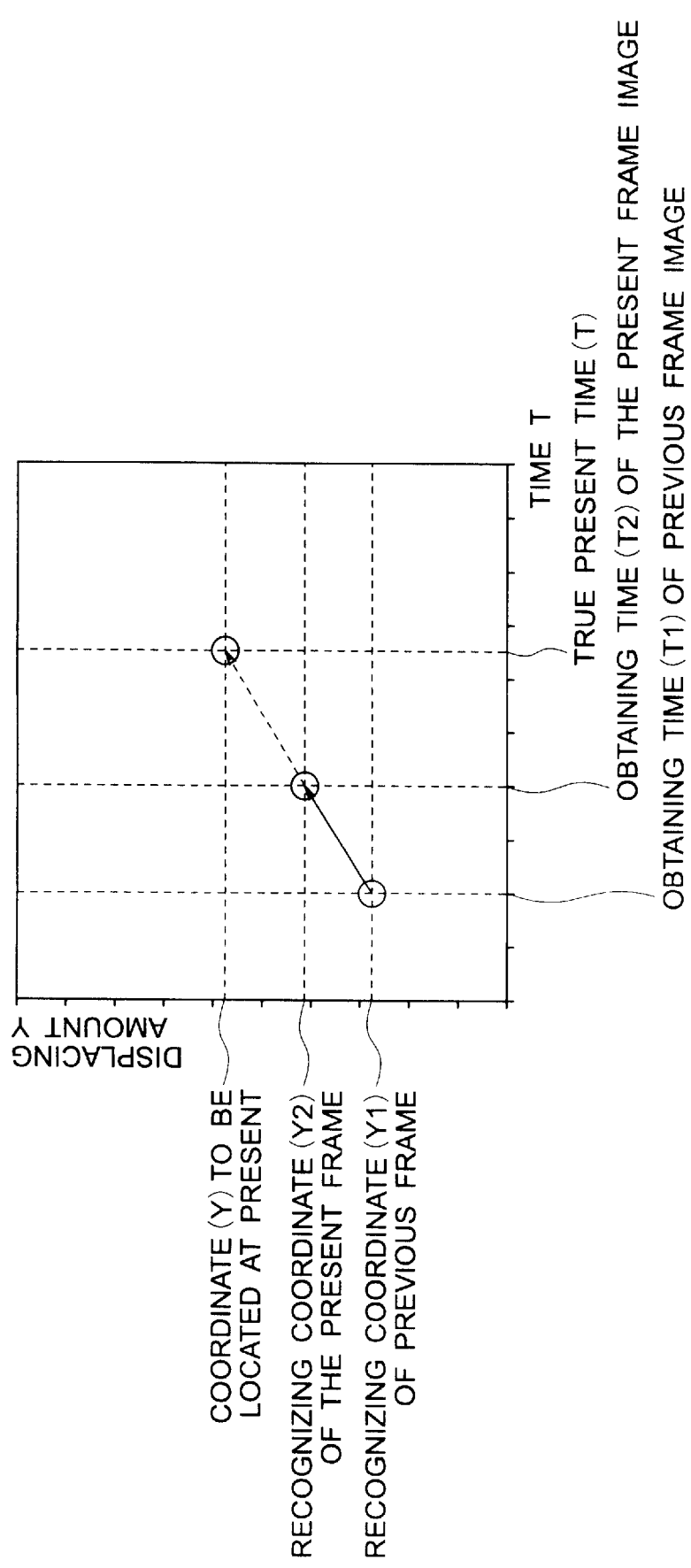
FIG. 17 is a view showing a position estimate in a moving body pursuit irradiating device in accordance with an embodiment 4 of this invention.

A moving body pursuit irradiating device in accordance with an embodiment 4 of this invention will be explained with reference to the drawings. FIG. 17 is a view showing a position estimate of the moving body pursuit irradiating device in accordance with the embodiment 4 of this invention.

In the above embodiment 1, the control of a medical treatment beam of the linac 15 is embodied by directly using three-dimensional coordinates obtained from a digitized fluoroscopic image. However, even if the fluoroscopic image is inputted at 30 frame/second, a delay of one frame is caused at its minimum until the three-dimensional coordinates are calculated and the medical treatment beam is controlled. Accordingly, a control error of the medical treatment beam is provided by multiplying this time by the moving speed of a tumor portion.

In contrast to this, as shown in FIG. 17, the moving speed of the tumor marker 17 is calculated from the three-dimensional coordinates of a fluoroscopic image just inputted and the position displacement of a fluoroscopic image in input timing previously set once. A moving amount multiplied by the above delay time is added as a position correcting amount. Thus, control accuracy of the medical treatment beam can be improved.

In FIG. 17, the true present time is provided by adding delays of digitizing and recognizing processings from the present frame image obtaining time. Accordingly, a coordinate to be located at present is expressed by the following formula.

$$y=y2+(y2-y1)*(t-t2)/(t2-t1)$$

Embodiment 5
(position estimate 2)

Figure 18:
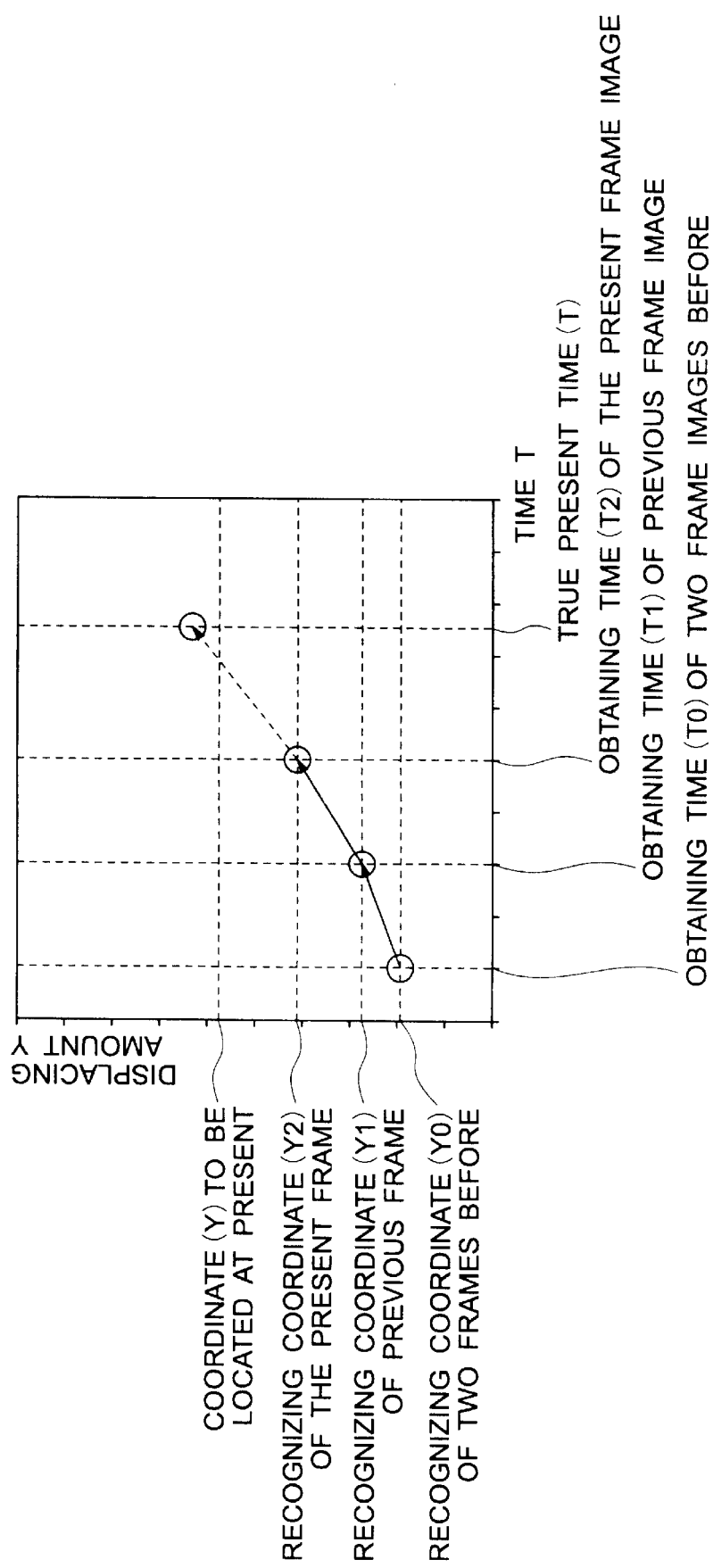
FIG. 18 is a view showing a position estimate 2 in a moving body pursuit irradiating device in accordance with an embodiment 5 of this invention.

A moving body pursuit irradiating device in accordance with an embodiment 5 of this invention will be explained with reference to the drawings. FIG. 18 is a view showing a position estimate of the moving body pursuit irradiating device in accordance with the embodiment 5 of this invention.

In the above embodiment 4, the moving speed of the tumor marker 17 is calculated from three-dimensional coordinates of a fluoroscopic image just inputted and the position displacement of a fluoroscopic image in input timing previously set once. A moving amount multiplied by the above delay time is added as a position correcting amount. Thus, control accuracy of the medical treatment beam can be improved. However, the moving speed of the tumor marker 17 can be calculated by further adding the position displacement of a fluoroscopic image in input timing previously set twice so that the position correcting amount of the above delay time can be more precisely calculated. Accordingly, the control accuracy of the medical treatment beam can be further improved.

In FIG. 18, the true present time is provided by adding delays of digitizing and recognizing processings from the present frame image obtaining time. When $\Delta t=t1-t0=t2-t1$, speed v1 at time t1, speed v2 at time t2 and acceleration a between these speeds are respectively provided as follows.

$$v1=(y1-y0)/\Delta t$$

$$v2=(y2-y1)/\Delta t$$

$$a=(y2-2 \cdot y1+y1)/(\Delta t)^2$$

Accordingly, a coordinate to be located at present is expressed by the following formula.

$$y=y2+v2*(t-t2)+a \cdot (t-t2)^2/2$$

Embodiment 6
(position control of medical treatment base)

Figure 19:
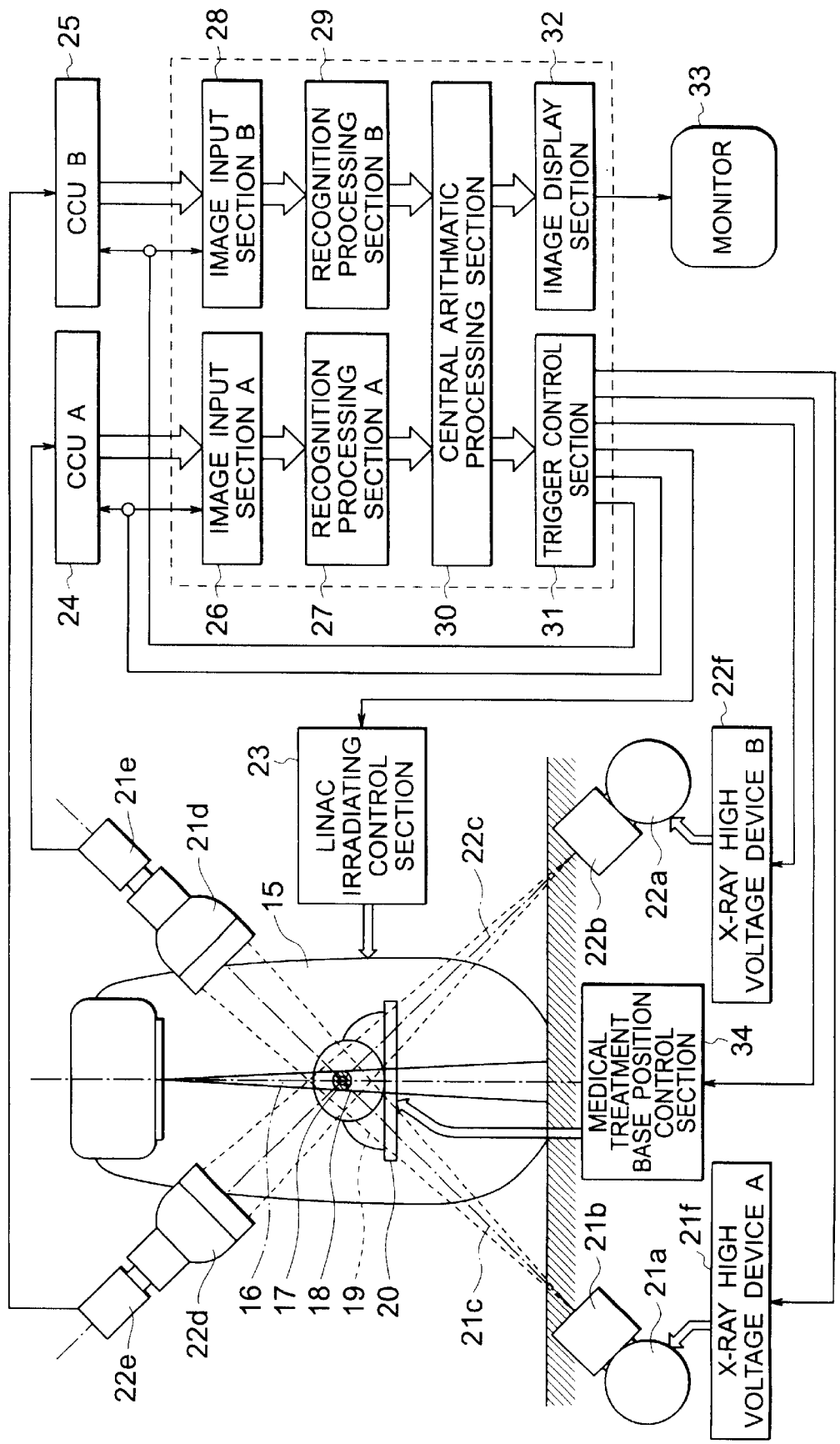
FIG. 19 is a view showing the construction of a moving body pursuit irradiating device in accordance with an embodiment 6 of this invention.

A moving body pursuit irradiating device in accordance with an embodiment 6 of this invention will be explained with reference to the drawings. FIG. 19 is a block diagram showing the construction of the moving body pursuit irradiating device in accordance with the embodiment 6 of this invention.

In FIG. 19, reference numeral 34 designates a medical treatment base position control section. The other constructions are similar to those in the above embodiment 1.

In the above embodiment 1, on/off control of the medical treatment beam 16 of the linac 15 is performed by obtained three-dimensional coordinates of the tumor marker 17. However, if the position of the medical treatment base is controlled such that this position is moved by the medical treatment base position control section 34 by performing an inverse operation from a moving amount of the tumor marker 17, the position of a tumor can be set to an irradiating object of the medical treatment beam at any time. Accordingly, unnecessary exposure due to a fluoroscope is restrained and a medical treatment time can be shortened.

Embodiment 7
(control of irradiating field by multi-leaf collimator)

Figure 20:
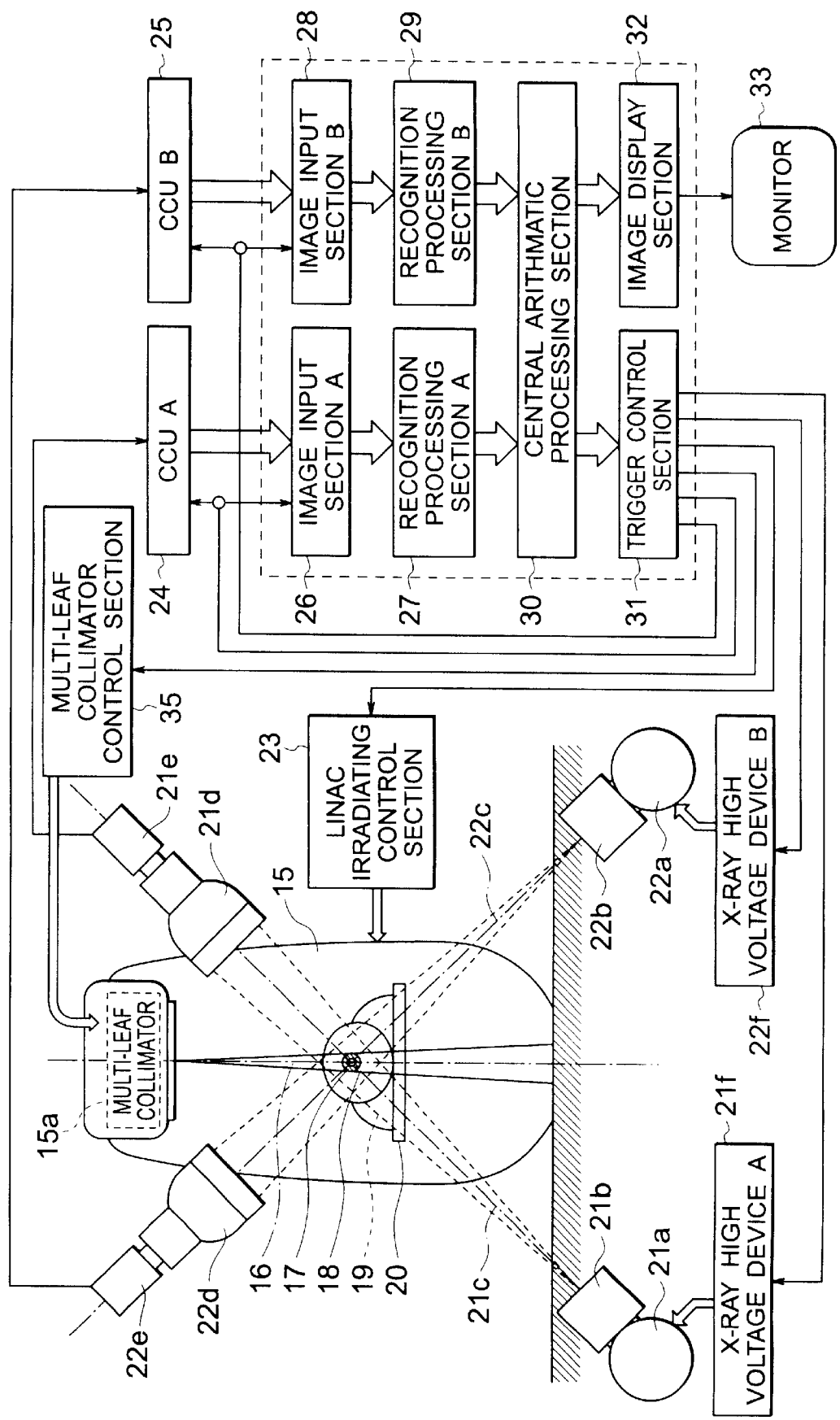
FIG. 20 is a view showing the construction of a moving body pursuit irradiating device in accordance with an embodiment 7 of this invention.

A moving body pursuit irradiating device in accordance with an embodiment 7 of this invention will be explained with reference to the drawings. FIG. 20 is a block diagram showing the construction of the moving body pursuit irradiating device in accordance with the embodiment 7 of this invention.

In FIG. 20, reference numerals 15a and 35 respectively designate a multi-leaf collimator and a multi-leaf collimator control section. The other constructions are similar to those in the above embodiment 1.

In the above embodiment 1, on/off control of the medical treatment beam 16 of the linac 15 is performed by obtained three-dimensional coordinates of the tumor marker 17. However, as shown in FIG. 20, if the moving body pursuit irradiating device is constructed such that the multi-leaf collimator 15a is opened and closed by the multi-leaf collimator control section 35 by performing an inverse operation from a moving amount of the tumor marker 17 and an irradiating field is dynamically controlled, the position of a tumor can be set to an irradiating object of the medical treatment beam at any time. Accordingly, unnecessary exposure due to a fluoroscope is restrained and a medical treatment time can be shortened.

Embodiment 8
(case using two tumor markers or more)

Figure 21:
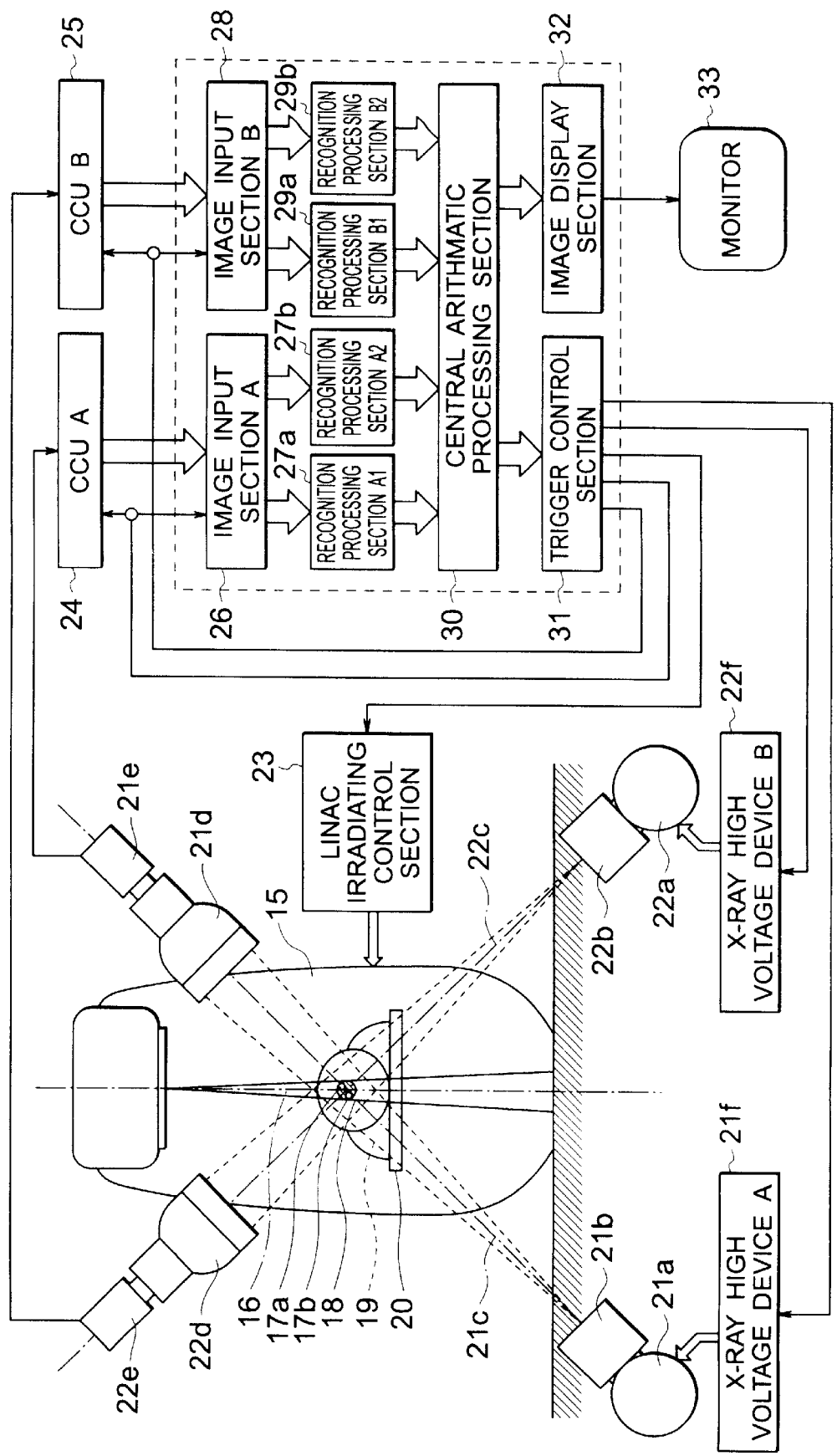
FIG. 21 is a view showing a case in which two tumor markers or more are used in a moving body pursuit irradiating device in accordance with an embodiment 8 of this invention.

A moving body pursuit irradiating device in accordance with an embodiment 8 of this invention will be explained with reference to the drawings. FIG. 21 is a block diagram showing the construction of the moving body pursuit irradiating device in accordance with the embodiment 8 of this invention.

In FIG. 21, each of reference numerals 17a and 17b designates a tumor marker. Reference numerals 27a and 27b respectively designate recognition processing sections A1 and A2. Reference numerals 29a and 29b respectively designate recognition processing sections B1 and B2. The other constructions are similar to those in the above embodiment 1.

In the above embodiment 1, one tumor marker is buried in the vicinity of a tumor. However, there is also a case in which two or three tumor markers are buried. In this case, recognition processing sections of images corresponding to the number of added tumor markers are required with respect to each fluoroscopic system. However, a tumor position can be specified even when the movement of a tumor 18 includes torsion and a rotating movement instead of a simple parallel displacement with respect to movements of the tumor markers 17a and 17b.

Embodiment 9
(blanking of image intensifier)

Figure 22:
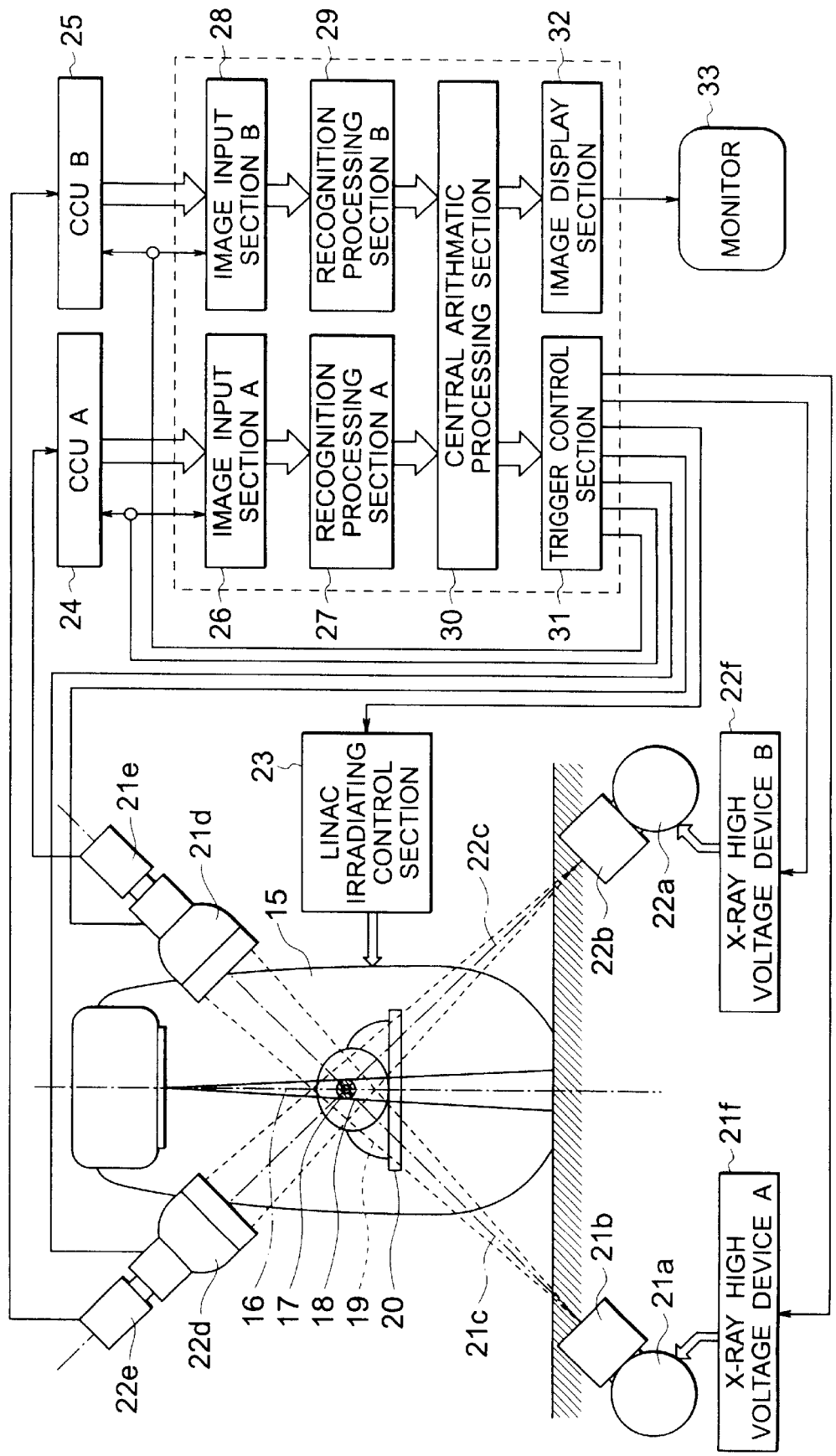
FIG. 22 is a view showing the construction of a moving body pursuit irradiating device in accordance with an embodiment 9 of this invention.
Figure 23:
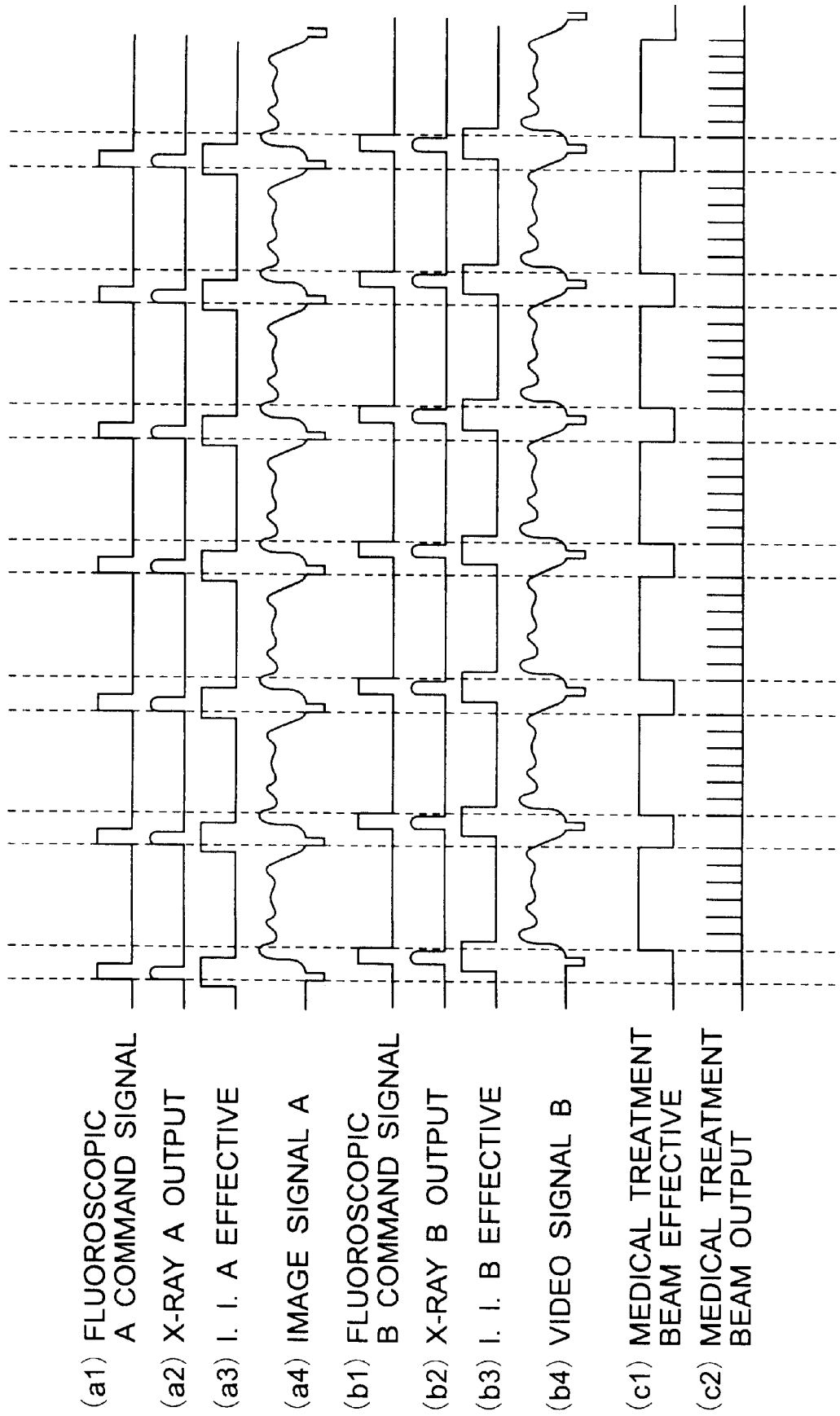
FIG. 23 is a timing chart showing an operation of the moving body pursuit irradiating device in accordance with the embodiment 9 of this invention.

A moving body pursuit irradiating device in accordance with an embodiment 9 of this invention will be next explained with reference to the drawings. FIG. 22 is a block diagram showing the construction of the moving body pursuit irradiating device in accordance with the embodiment 9 of this invention. FIG. 23 is a timing chart showing an operation of the moving body pursuit irradiating device in accordance with the embodiment 9 of this invention.

In FIG. 22, image intensifiers A and B (21d and 22d) are connected to a trigger control section 31. The other construction are similar to those in the above embodiment 1.

In the above embodiment 1, no special processing is performed with respect to the output control of an X-ray. However, in this embodiment, as shown in FIGS. 23(a2) and 23(b2), X-rays of X-ray tubes 21a and 22a are irradiated in a pulse shape in synchronization with frame rates of TV cameras 21e and 22e. Further, as shown in FIG. 23(c2), the output control is performed such that no medical treatment beam 16 of the linac 15 is irradiated in irradiating timings of the X-ray tubes 21a and 22a.

Further, as shown in FIGS. 23(a3) and 23(b3), the operation of the moving body pursuit irradiating device is controlled such that outputs of the image intensifiers 21d and 22d are effective only in the irradiating timings of the X-ray tubes 21a and 22a. Thus, the present invention has an effect that it is possible to greatly reduce a rise in background level of a fluoroscopic image due to a large amount of scattering radiation generated by the linac 15.

Embodiment 10
(application to head portion)

Figure 24:
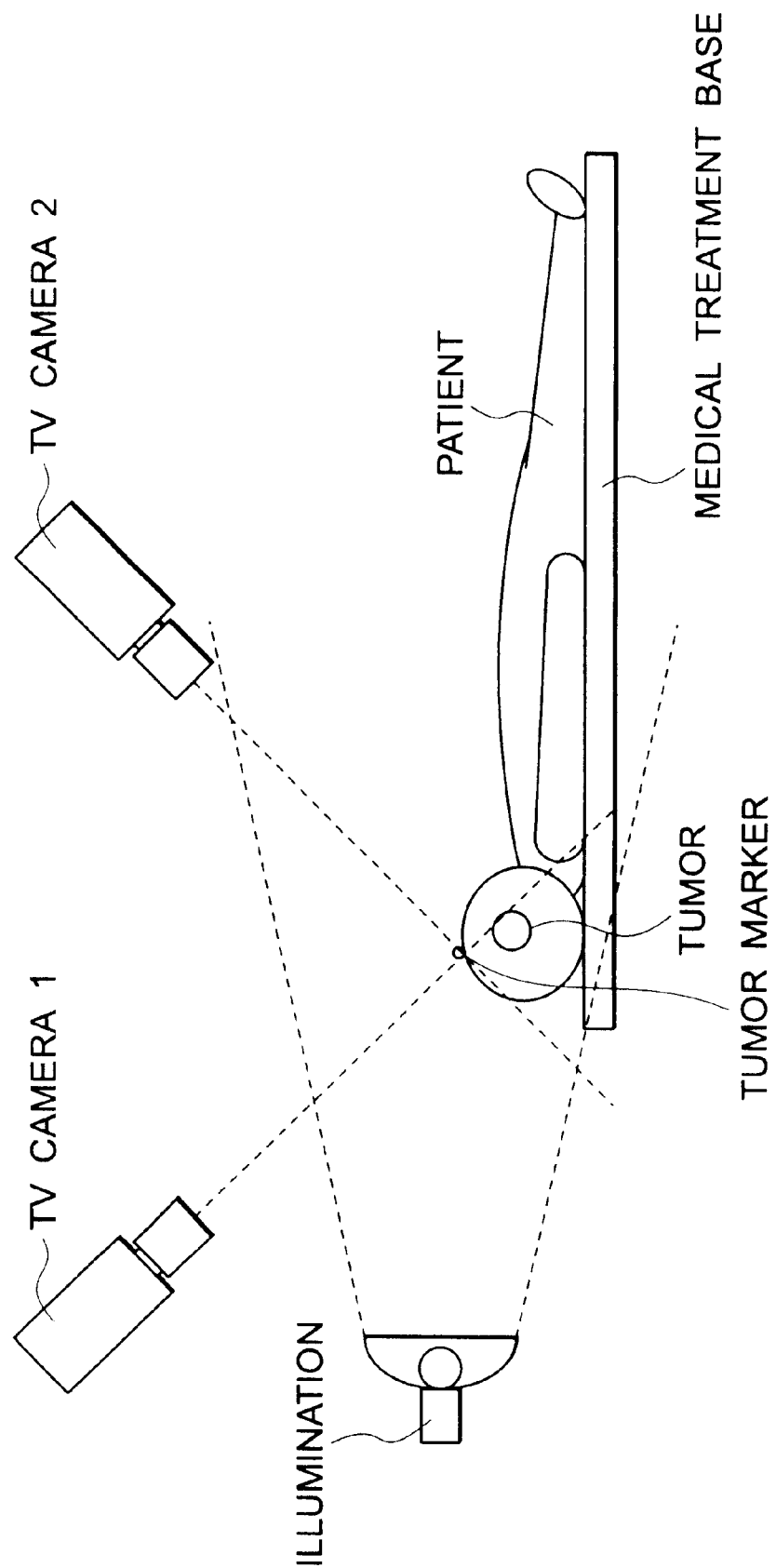
FIG. 24 is a view showing that a moving body pursuit irradiating device in accordance with an embodiment 10 of this invention is applied to a head portion.

A moving body pursuit irradiating device in accordance with an embodiment 10 of this invention will be explained with reference to the drawings. FIG. 24 is a view showing the construction of the moving body pursuit irradiating device in accordance with the embodiment 10 of this invention. The other constructions in FIG. 24 are similar to those in the above embodiment 1.

In the above embodiment 1, the tumor marker 17 is buried in the vicinity of a tumor to directly monitor a movement of the tumor within a body, and fluoroscopic images are obtained by two fluoroscopes and three-dimensional coordinates are calculated. However, in this embodiment, as shown in FIG. 24, a TV camera using a visible ray is used instead of an X-ray fluoroscope in a portion in which it is considered that no tumor is almost moved as in a head portion tumor with respect to a body surface.

Effects similar to those in the above embodiment 1 are obtained by sticking a marker having a surface color having a high absorbing property with respect to a visible ray to the surface of a head portion instead of a construction in which the tumor marker is opaque with respect to the X-ray. In this case,-unnecessary exposure to the X-ray irradiated from the fluoroscope can be removed.

Embodiment 11
(optimization of medical treatment position using prediagnosis)

Figure 25:
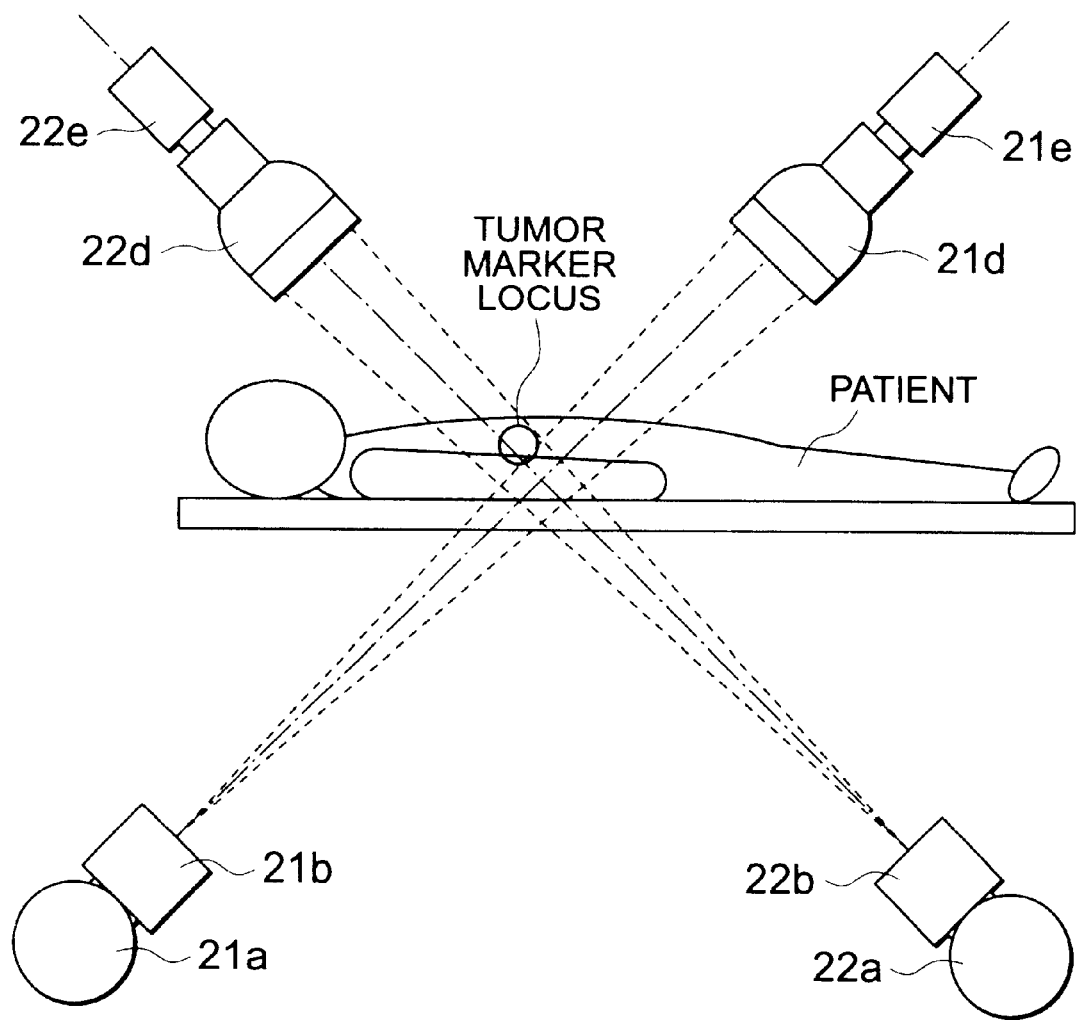
FIG. 25 is a view showing the optimization of a medical treatment position in prediagnosis of a moving body pursuit irradiating device in accordance with an embodiment 11 of this invention.

A moving body pursuit irradiating device in accordance with an embodiment 11 of this invention will be explained with reference to the drawings. FIG. 25 is a view showing a situation of the moving body pursuit irradiating device in accordance with the embodiment 11 of this invention. The construction in this embodiment is similar to that in the above embodiment 1.

In the above embodiment 1, the operation of the moving body pursuit irradiating device is controlled such that the medical treatment beam 16 of the linac 15 is irradiated when the tumor marker 17 is located in a position planned in advance. However, in accordance with the construction of the above embodiment 1, image input timing is provided by about 30 frame/second and three-dimensional coordinates of the tumor marker 17 are calculated every input of one frame. In this embodiment, a frequency distribution of the three-dimensional coordinates of the tumor marker 17 can be calculated by performing a monitoring operation for about several seconds to several ten seconds before a medical treatment. If the operation of a linac irradiating control section 23 is controlled such that a high frequency area of the central arithmetic processing section 30 among the obtained frequency distributions is set to a medical treatment portion, unnecessary exposure due to a fluoroscope is restrained and a medical treatment time can be shortened.

Embodiment 12
(case using plural X-ray fluoroscopes)

Figure 26:
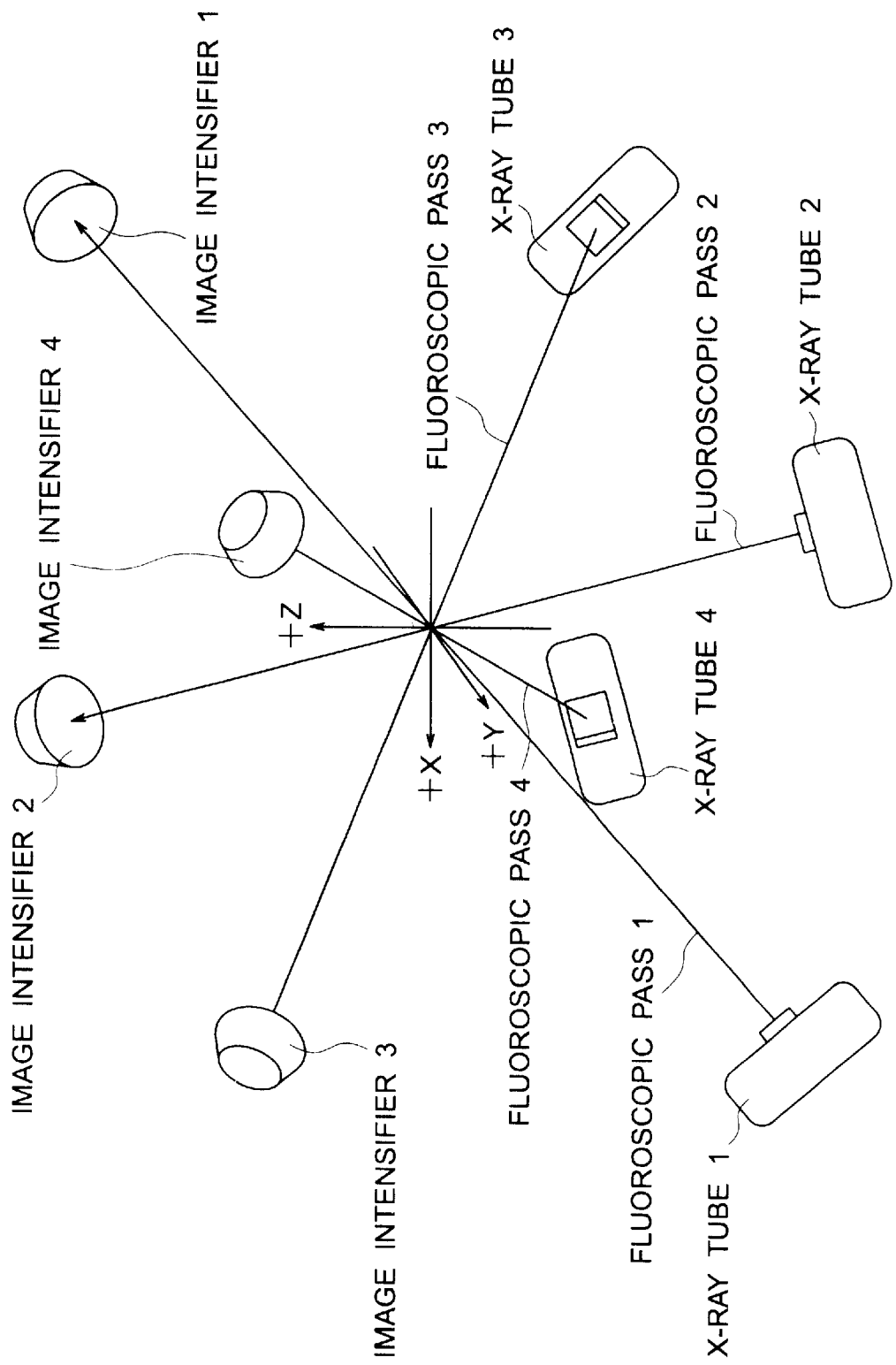
FIG. 26 is a view showing the construction of a moving body pursuit irradiating device in accordance with an embodiment 12 of this invention.
Figure 27:
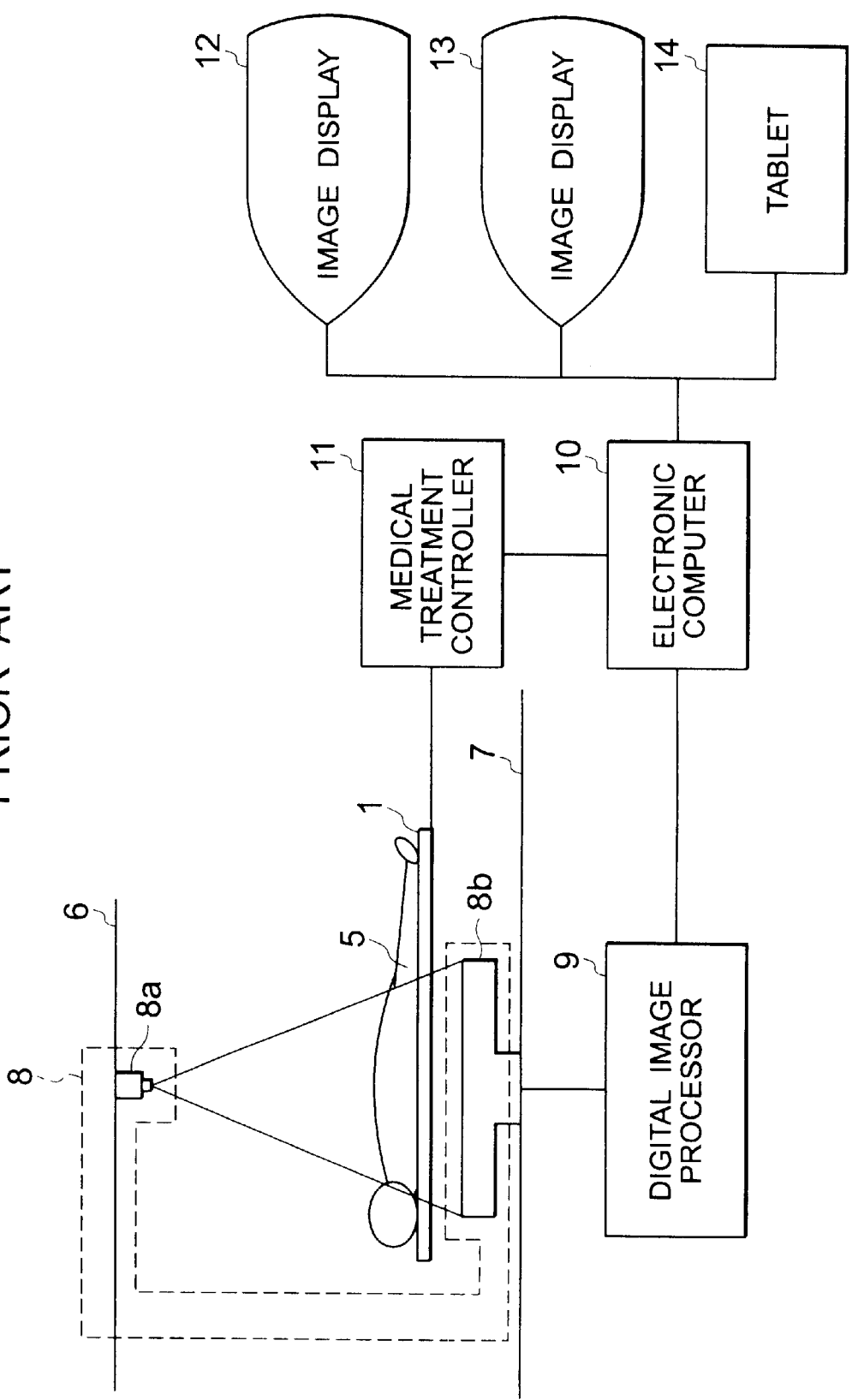
FIG. 27 is a view showing the construction of a conventional moving body pursuit irradiating device.
Figure 28:
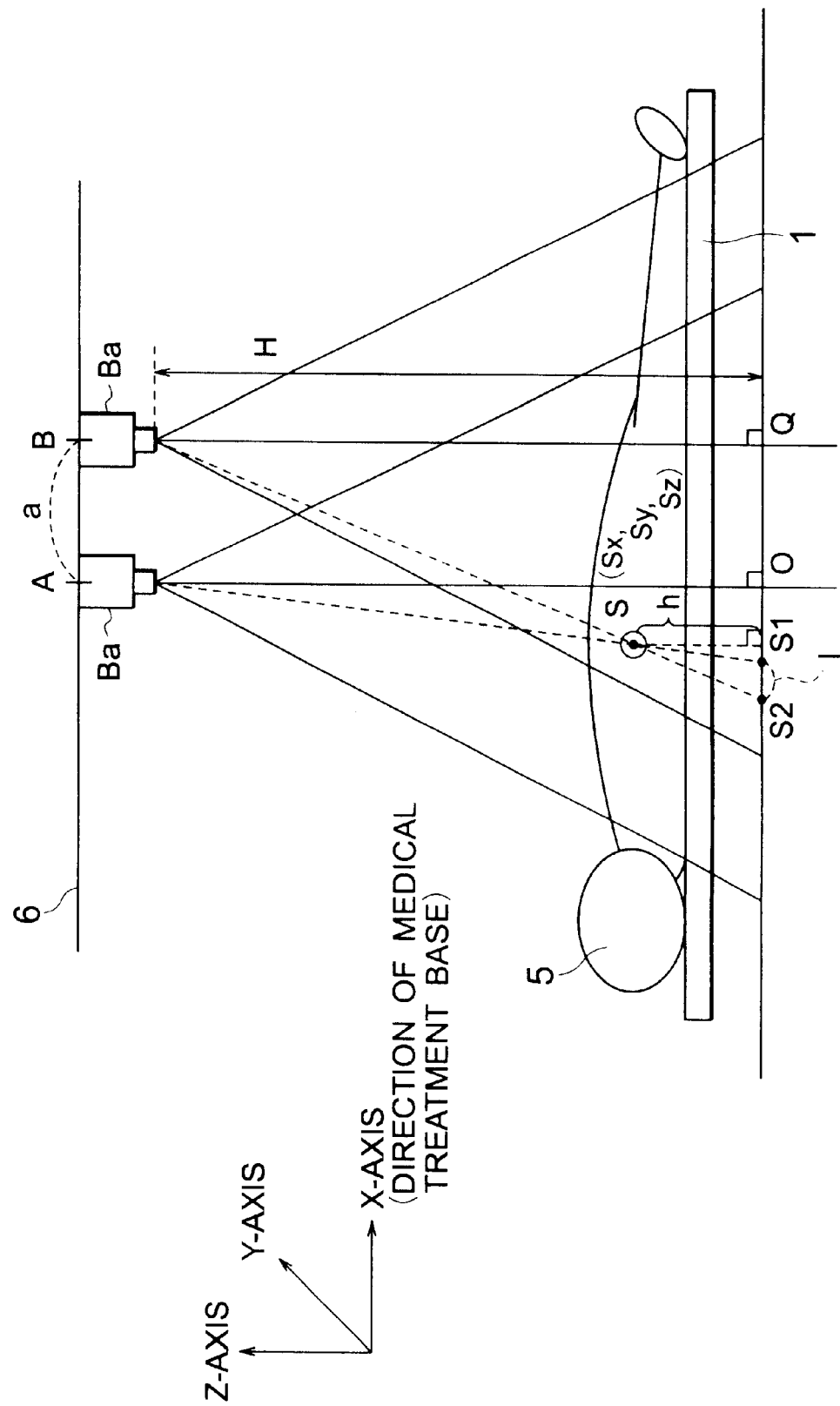
FIG. 28 is a view showing an operation of the conventional moving body pursuit irradiating device.
Figure 29A:
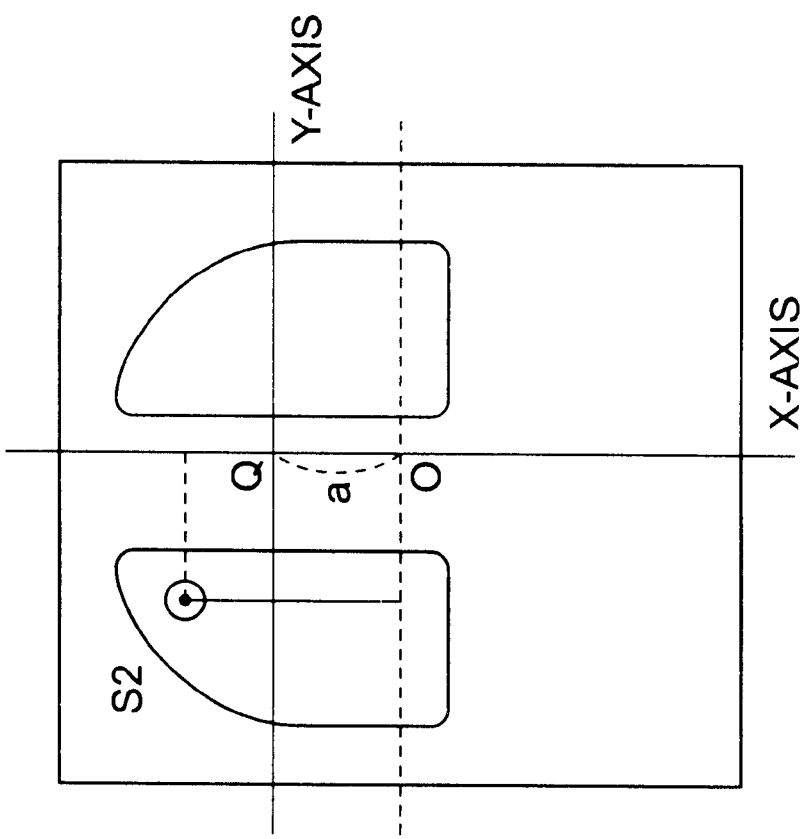
FIG. 29A–29B are views showing the operation of the conventional moving body pursuit irradiating device.
Figure 29B:
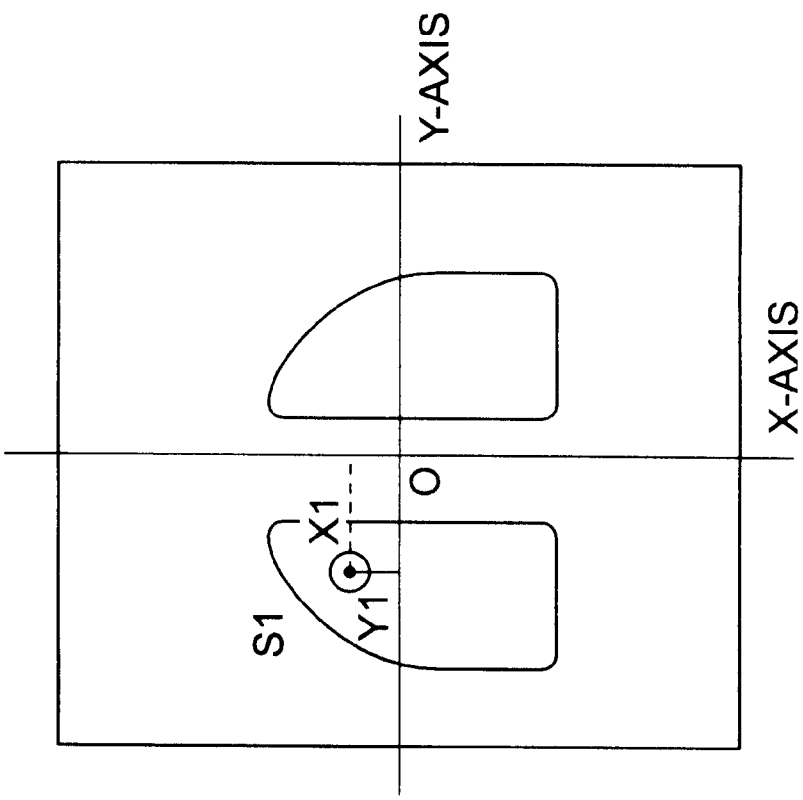

A moving body pursuit irradiating device in accordance with an embodiment 12 of this invention will be explained with reference to the drawings. FIG. 26 is a view showing the construction of the moving body pursuit irradiating device in accordance with the embodiment 12 of this invention. The other constructions in FIG. 26 are similar to those in the above embodiment 1.

In the above embodiment 1, two fluoroscopic systems are used. However, as shown in FIG. 26, one or two fluoroscopic systems may be further added. In this case, two fluoroscopic systems among plural fluoroscopic systems are set to simultaneously function. The linac 15 variously sets a gantry angle to change directions and orientations of the medical treatment beam 16. However, when the linac 15 interferes with an X-ray pass of a certain fluoroscopic system, three-dimensional coordinates of the tumor marker 17 can be calculated by combining separate fluoroscopic systems which do not interfere with each other. Namely, the central arithmetic processing section 30 selectively uses two uninterfering fluoroscopic systems among the plural fluoroscopic systems on the basis of the obtained gantry angle.

What is claimed is:
1. A moving body pursuit irradiating device comprising:
   a linac for irradiating a medical treatment beam to a tumor;
   a tumor marker buried in the vicinity of the tumor;
   a first X-ray fluoroscope for picking up an image of said tumor marker from a first direction;
   a second X-ray fluoroscope for picking up the image of said tumor marker from a second direction at the same time as said first X-ray fluoroscope;
   first and second image input sections for digitizing first and second fluoroscopic images outputted from said first and second X-ray fluoroscopes;
   first and second recognition processing sections which execute template matching at a real time level at a predetermined frame rate by a shading normalization mutual correlation method for applying a template image of the tumor marker registered in advance to image information digitized by said first and second image input sections, and calculate first and second two-dimensional coordinates of said tumor marker;
   a central arithmetic processing section for calculating three-dimensional coordinates of said tumor marker from the first and second two-dimensional coordinates calculated by said first and second recognition processing sections; and
   an irradiating control section for controlling the irradiation of the medical treatment beam of said linac by said calculated three-dimensional coordinates of the tumor marker.

2. A moving body pursuit irradiating device as claimed in claim 1, wherein
    each of said first and second X-ray fluoroscopes intermittently picks up the image of said tumor marker when it is known that a moving speed of said tumor is low.

3. A moving body pursuit irradiating device as claimed in claim 1, wherein
    each of said first and second recognition processing sections limits an input image area for embodying the template matching when a maximum speed of said tumor marker can be estimated.

4. A moving body pursuit irradiating device as claimed in claim 1, wherein
    said central arithmetic processing section calculates a moving speed of said tumor marker from the three-dimensional coordinates of a fluoroscopic image just inputted and the position displacement of a fluoroscopic image in input timing previously set once, and adds a moving amount multiplied by a delay time provided by a series of processings to a recognizing coordinate of the present frame as a position correcting amount.

5. A moving body pursuit irradiating device as claimed in claim 1, wherein
    said central arithmetic processing section calculates a moving acceleration of said tumor marker from the three-dimensional coordinates of a fluoroscopic image just inputted and the position displacement of a fluoroscopic image in each of input timings previously set once and twice, and adds a position correcting amount corresponding to a delay time provided by a series of processings to a recognizing coordinate of the present frame.

6. A moving body pursuit irradiating device as claimed in claim 1, further comprising a medical treatment base position control section for controlling the position of a medical treatment base such that this position of the medical treatment base is moved by performing an inverse operation from a moving amount of said tumor marker on the medical treatment base.

7. A moving body pursuit irradiating device as claimed in claim 1, further comprising a multi-leaf collimator control section for dynamically controlling an irradiating field by opening and closing a multi-leaf collimator arranged in said linac by performing an inverse operation from a moving amount of said tumor marker.

8. A moving body pursuit irradiating device as claimed in claim 1, wherein
    a plurality of said tumor markers are included.

9. A moving body pursuit irradiating device as claimed in claim 1, wherein
    said central arithmetic processing section performs a control operation such that the X-ray of each of said first and second X-ray fluoroscopes is irradiated in a pulse shape by a trigger control section in synchronization with said predetermined frame rate, and no medical treatment beam of said linac is irradiated in irradiating timing of each of said first and second x-ray fluoroscopes.

10. A moving body pursuit irradiating device as claimed in claim 1, wherein
    said tumor marker has a surface color having a high absorbing property with respect to a visible ray and is stuck to the surface of a head portion instead of burying of the tumor marker in the vicinity of the tumor, and
    first and second TV cameras using a visible ray are used instead of said first and second X-ray fluoroscopes.

11. A moving body pursuit irradiating device as claimed in claim 1, wherein
    said central arithmetic processing section calculates a frequency distribution of the three-dimensional coordinates of said tumor marker by performing a monitoring operation for a predetermined time before a medical treatment is taken, and controls an operation of said irradiating control section such that a high frequency area is set to a medical treatment portion.

12. A moving body pursuit irradiating device as claimed in claim 1, further comprising a third X-ray fluoroscope for picking up the image of said tumor marker from a third direction is arranged, wherein said central arithmetic processing section selectively uses two uninterfering X-ray fluoroscopes among the first, second and third X-ray fluoroscopes on the basis of an obtained gantry angle.

13. A positioning method using a moving body pursuit irradiating device, comprising the steps of:
    obtaining first and second fluoroscopic images by simultaneously picking up the image of a tumor marker buried in the vicinity of a tumor from first and second directions;
    executing template matching at a real time level at a predetermined frame rate by a shading normalization mutual correlation method for applying a template image of the tumor marker registered in advance to first and second digitized fluoroscopic images, and calculating first and second two-dimensional coordinates of said tumor marker on the basis of first and second fluoroscopic transformation matrices;
    calculating three-dimensional coordinates of said tumor maker on the basis of said first and second calculated two-dimensional coordinates; and
    positioning the medical treatment beam of a linac on the basis of said calculated three-dimensional coordinates of the tumor marker.

14. A positioning method using a moving body pursuit irradiating device as claimed in claim 13, further comprising the steps of:
    obtaining third and fourth fluoroscopic images by simultaneously picking up the image of a spatial coordinate calibrator arranged at an isocenter from the first and second directions in advance; and
    calculating said first and second fluoroscopic transformation matrices in advance by commands of six vertexes of said spatial coordinate calibrator displayed on said third and fourth fluoroscopic images.

* * * * *